US012768830B2

(12) United States Patent
Agarwal et al.

(10) Patent No.: US 12,768,830 B2
(45) Date of Patent: Oct. 20, 2026

(54) METHODS AND SYSTEMS FOR RAPID DETECTION OF COVID-19

(71) Applicant: The Trustees of Indiana University, Bloomington, IN (US)

(72) Inventors: Mangilal Agarwal, Bloomington, IN (US); Amanda Siegel, Bloomington, IN (US); Mark David Woollam, Bloomington, IN (US); Paula Andrea Angarita-Rivera, Bloomington, IN (US)

(73) Assignee: The Trustees of Indiana University, Bloomington, IN (US)

( * ) Notice: Subject to any disclaimer, the term of this patent is extended or adjusted under 35 U.S.C. 154(b) by 313 days.

(21) Appl. No.: 18/580,854

(22) PCT Filed: Jul. 21, 2022

(86) PCT No.: PCT/US2022/037824
§ 371 (c)(1),
(2) Date: Jan. 19, 2024

(87) PCT Pub. No.: WO2023/004010
PCT Pub. Date: Jan. 26, 2023

(65) Prior Publication Data

US 2025/0110112 A1 Apr. 3, 2025

Related U.S. Application Data

(60) Provisional application No. 63/224,306, filed on Jul. 21, 2021.

(51) Int. Cl.
*G01N 33/49* (2006.01)
*G01N 33/497* (2006.01)
(Continued)

(52) U.S. Cl.
CPC ..... *G01N 33/4977* (2024.05); *G01N 33/6848* (2013.01); *G16H 50/20* (2018.01)

(58) Field of Classification Search
None
See application file for complete search history.

(56) References Cited

U.S. PATENT DOCUMENTS

2020/0337594 A1* 10/2020 Reddy .................... A61B 5/082

FOREIGN PATENT DOCUMENTS

WO WO-2021028928 A1 * 2/2021 ....... G01N 33/56983

OTHER PUBLICATIONS

Angle, C., Waggoner, L. P., Ferrando, A., Haney, P. & Passler, T. Canine Detection of the Volatilome: A Review of Implications for Pathogen and Disease Detection. 3, doi:10.3389/fvets.2016.00047 (2016).

(Continued)

*Primary Examiner* — Eric S. McCall
*Assistant Examiner* — Nigel H Plumb
(74) *Attorney, Agent, or Firm* — Taft Stettinius & Hollister LLP

(57) ABSTRACT

Methods for diagnosing a subject for a COVID-19 infection state include collecting an alveolar air breath sample from a subject; passing the breath sample into contact with a volatile organic compound (VOC) sensor operable to detect a plurality of VOC biomarkers for a COVID-19 infection state; producing a readable sensor output for at least two of the plurality of biomarkers; and diagnosing the COVID-19 infection state of the subject based on the readable sensor output. Systems for detecting and identifying at least one VOC biomarker for a COVID-19 infection state in exhaled breath of a subject include a mouth piece connected to a housing, the mouth piece operable to receive the exhaled breath of the subject; a sensor module disposed in the (Continued)

housing, the sensor module operable to detect the at least one VOC biomarker in the exhaled breath, and further operable to produce a readable sensor output for the at least one VOC biomarker; and a communication module disposed in the housing and in communication with the sensor module, the communication module operable to transmit collected data from the sensor module.

20 Claims, 8 Drawing Sheets

(51) Int. Cl.
*G01N 33/68* (2006.01)
*G16H 50/20* (2018.01)

(56) References Cited

OTHER PUBLICATIONS

Jezierski, T., Walczak, M., Ligor, T., Rudnicka, J. & Buszewski, B. Study of the art: canine olfaction used for cancer detection on the basis of breath odour. Perspectives and limitations. Journal of breath research 9, 027001, doi:10.1088/1752-7155/9/2/027001 (2015).
Janfaza, S., Khorsand, B., Nikkhah, M. & Zahiri, J. Digging deeper into volatile organic compounds associated with cancer. Biology methods & protocols 4, bpz014, doi:10.1093/biomethods/bpz014 (2019).
Linebaugh, K. Service Dogs Pick Up Scent of Diabetes Danger. Wall Street Journal (2012).
Oakley-Girvan, I. & Davis, S. W. Breath based volatile organic compounds in the detection of breast, lung, and colorectal cancers: A systematic review. Cancer Biomarkers 21, 29-39, doi:10.3233/CBM-170177 (2018).
Traxler, S. et al. VOC breath profile in spontaneously breathing awake swine during Influenza A infection. Scientific reports 8, 14857, doi: 10.1038/s41598-018-33061-2 (2018).
Ruszkiewicz, D. M. et al. Diagnosis of COVID-19 by analysis of breath with gas chromatography-ion mobility spectrometry—a feasibility study. EClinicalMedicine 29, doi: 10.1016/j.eclinm.2020.100609 (2020).
Wilson, A. D. Applications of Electronic-Nose Technologies for Noninvasive Early Detection of Plant, Animal and Human Diseases. 6, 45 (2018).
Tan, J. K. et al. The prevalence and clinical significance of Presymptomatic COVID-19 patients: how we can be one step ahead in mitigating a deadly pandemic. BMC Infectious Diseases 21, 249, doi: 10.1186/s12879-021-05849-7 (2021).
Lamote, K. et al. The scent of COVID-19: viral (semi-)volatiles as fast diagnostic biomarkers? Journal of breath research 14, 042001, doi: 10.1088/1752-7163/aba105 (2020).
Fu, D et al. Polymer coated silicon microring device for the detection of sub-ppm volatile organic compounds. Sensors and Actuators B: Chemical 257, 136-142, doi:https://doi.org/10.1016/j.snb.2017.10.166 (2018).
Mgwenya, T. N. Polymer nanocomposites-based sensors for the detection of lung cancer volatile organic biomarkers, University of Johannesburg, (2018).
Ŝetka, M., Drbohlavová, J. & Hubálek, J. Nanostructured Polypyrrole-Based Ammonia and Volatile Organic Compound Sensors. Sensors (Basel) 17, 562, doi:10.3390/s17030562 (2017).
Yavarinasab, A. et al. Graphene/poly (methyl methacrylate) electrochemical impedance-transduced chemiresistor for detection of volatile organic compounds in aqueous medium. Anal Chim Acta 1109, 27-36, doi:10.1016/j.aca.2020.02.065 (2020).
Bhattacharyya, D., Kumar, P., Smith, Y. R., Mohanty, S. K. & Misra, M. Plasmonic-enhanced electrochemical detection of volatile biomarkers with gold functionalized TiO2 nanotube arrays. Journal of Materials Science & Technology 34, 905-913, doi:https://doi.org/10.1016/j.jmst.2017.11.010 (2018).
Park, C. H., Schroeder, V., Kim, B. J. & Swager, T. M. Ionic Liquid-Carbon Nanotube Sensor Arrays for Human Breath Related Volatile Organic Compounds. ACS Sens 3, 2432-2437, doi: 10.1021/acssensors.8b00987 (2018).
Prasongkit, J., Tangsukworakhun, S., Jaisutti, R. & Osotchan, T. Highly sensitive and selective sensing of acetone and hydrogen sulfide using metal phthalocyanine—carbon nanotube hybrids. Applied Surface Science 532, 147314, doi: https://doi.org/10.1016/j.apsusc.2020.147314 (2020).
Sachan, A., Castro, M., Choudhary, V. & Feller, J.-F. Influence of Water Molecules on the Detection of Volatile Organic Compounds (VOC) Cancer Biomarkers by Nanocomposite Quantum Resistive Vapor Sensors vQRS. 6, 64 (2018).
Matatagui, D. et al. Chemoresistive gas sensor based on ZIF-8/ZIF-67 nanocrystals. Sensors and Actuators B: Chemical 274, 601-608, doi:https://doi.org/10.1016/j.snb.2018.07.137 (2018).
Wang, D. et al. Bimetallic PtCu Nanocrystal Sensitization WO(3) Hollow Spheres for Highly Efficient 3-Hydroxy-2-butanone Biomarker Detection. ACS Appl Mater Interfaces 12, 18904-18912, doi:10.1021/acsami.0c02523 (2020).
Bahoumina, P. et al. in 2017 Symposium on Design, Test, Integration and Packaging of MEMS/MIEMS (DTIP). 1-4.
Tung, T. T. et al. Carbon nanomaterial sensors for cancer and disease diagnosis. 167-202 (2019).
International Search Report; International Searching Authority; International Application No. PCT/US2022/037824; Dec. 19, 2022; 5 pages.
Written Opinion of the International Searching Authority; International Searching Authority; International Application No. PCT/US2022/037824; Dec. 19, 2022; 11 pages.

* cited by examiner

METHODS AND SYSTEMS FOR RAPID DETECTION OF COVID-19

CROSS-REFERENCE TO RELATED APPLICATION

This application is a U.S. National Phase Entry of International PCT Application No. PCT/US2022/037824 filed on Jul. 21, 2022, which claims priority to U.S. Provisional Patent Application No. 63/224,306, which was filed Jul. 21, 2021, the entire content of which is incorporated herein by reference.

STATEMENT ON FEDERALLY SPONSORED RESEARCH OR DEVELOPMENT

This invention was made with government support under 1502310 awarded by National Science Foundation. The government has certain rights in the invention.

BACKGROUND

The present disclosure relates generally to identification and/or detection of certain substances in the exhaled breath of a subject, and more particularly to systems, methods, and devices for identifying and/or detecting volatile organic compound ("VOC") biomarkers associated with SARS-CoV-2 (also referred to herein as "COVID-19") infection in the exhaled breath of a subject in real-time to diagnose a COVID-19 disease state.

Timely detection of health conditions can provide potentially life-saving information to patients. Human breath has been shown to contain VOC biomarkers that can be used to identify certain diseases. These VOCs allow for many potential applications of noninvasive detection of diseases and other biological metrics. For example, acetone levels in breath are a significant indicator of the presence of diabetes, a disease that threatens the lives of millions of people in the US and around the world, and ethanol also has been shown to have potential medical applications for diabetes detection. Moreover, links have been reported between breath isoprene level and oxidative stress, blood cholesterol level, and increased breath and heart rate. Esters similar to 2-ethylhexyl acetate are common in breath and have been linked to multiple diseases, including lung cancer.

COVID-19, a disease caused by severe acute respiratory distress syndrome (ARDS), is a current ongoing worldwide pandemic that has resulted in tens of millions of cases in the worldwide population. After SARS-CoV and MERS-CoV, COVID-19 is the third zoonotic origin virus with the only pandemic level. Persons infected by the COVID-19 virus, which may be found in the lungs, kidneys, heart, and intestines, may develop severe pneumonia, along with ARDS, and commonly exhibit symptoms caused by the flu, such as dry cough, chest tightness, and fever, for example.

The COVID-19 pandemic has shed light on the need for rapidly deployable noninvasive biomedical diagnostic assays for viral pathogens that are both fast and accurate and has awakened the need for advancement in technologies for rapid detection/diagnosis of infected persons, including early diagnosis of infection prior to the onset of classical symptoms. Pre-symptomatic COVID-19 patients have been a major stumbling block to break the chain of transmission, as viral shedding has been reported to peak 1-2 days prior to symptom onset. The current diagnostic gold standard is reverse transcription coupled to the polymerase chain reaction (RT-PCR). While highly accurate, these tests take at least a few hours, if not days, to generate a result and they are rarely utilized for testing asymptomatic (or pre-symptomatic) patients.

There remains a need for solutions to the above problems, including a need for systems, methods and devices for rapid, noninvasive point-of-care testing to diagnose viral diseases including COVID-19, influenza, and other transmissible diseases with high accuracy regardless of the presence of classical symptoms. Also needed is the creation of an adaptable sensor system and associated methodology which enables the quick translation of known cases of disease into a diagnostic test for emerging viruses that arise in the future. The present disclosure addresses these needs.

SUMMARY

The present disclosure provides systems, methods, processes and devices for correlating VOC biomarkers to a COVID-19 positive disease state and using the VOC biomarkers for rapid diagnosis of COVID-19 infection in a subject.

In one aspect of the disclosure, there are provided methods for identifying VOCs that are present in the breath of a subject with a COVID-19 Positive disease state. In one embodiment, VOCs associated with a COVID-19 Positive disease state are identified and/or patterns or biosignatures representing a COVID-19 Positive disease state are developed using a SPME GC-MS QTOF method. In some embodiments, methods utilize VOC sensor data to develop patterns or biosignatures representing a COVID-19 Positive disease state.

In another aspect, the disclosure provides methods for diagnosing a subject for a COVID-19 infection state.

In some embodiments, the methods include: (i) collecting an alveolar air breath sample from a subject; (ii) passing the breath sample into contact with a volatile organic compound (VOC) sensor operable to detect at least one VOC biomarker for a COVID-19 infection state; (iii) producing a readable sensor output for the at least one VOC biomarker; and (iv) diagnosing the COVID-19 infection state of the subject based on the readable sensor output. In other embodiments, the methods further include: (v) determining a correlation between the readable sensor output and a predefined signal or signal pattern associated with the COVID-19 infection state; and (vi) identifying, based at least in part on the determination of a correlation with the predefined signal or signal pattern, the presence of the COVID-19 infection state. In some embodiments, the methods further include: (v) processing the readable sensor output via a neural network or pattern recognition algorithm, wherein the readable sensor output correlates with a predefined signal or signal pattern associated with the COVID-19 infection state; and (vi) identifying, based at least in part on the determination of a correlation with the predefined signal or signal pattern, the presence of the COVID-19 infection state.

In another aspect, the disclosure provides a system for detecting and identifying at least one VOC biomarker for a COVID-19 infection state in exhaled breath of a subject, the system comprising: a mouth piece connected to a housing, the mouth piece operable to receive the exhaled breath of the subject; a sensor module disposed in the housing, the sensor module operable to detect the at least one VOC biomarker in the exhaled breath, and further operable to produce a readable sensor output for the at least one VOC biomarker; and a communication module disposed in the housing and in communication with the sensor module, the communication module operable to transmit collected data from the sensor module.

In some embodiments, the system further includes a biomarker processing module in communication with the sensor module, the biomarker processing module operable to process the collected data associated with detection of the at least one VOC biomarker and to identify the at least one VOC biomarker.

This summary is not intended to identify key or essential features of the claimed subject matter, nor is it intended to be used as an aid in limiting the scope of the claimed subject matter. These and other features of the present disclosure will become more apparent from the following description of the illustrative embodiments.

BRIEF DESCRIPTION OF THE DRAWINGS

Various concepts and embodiments described herein are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION

Figure 1:
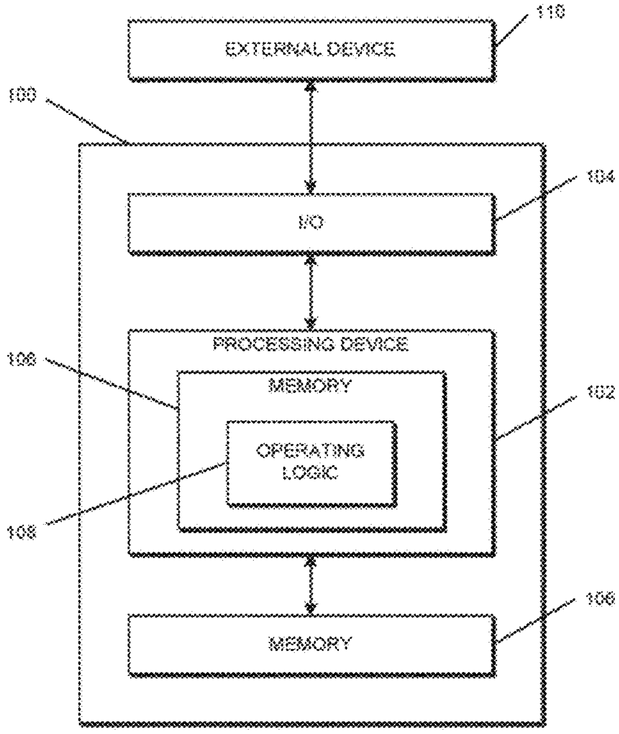
FIG. 1 is a simplified block diagram of one embodiment of a computing device.

While the concepts of the present disclosure are susceptible to various modifications and alternative forms, specific embodiments thereof are shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Unless defined otherwise, all technical and scientific terms used in this disclosure have the same meaning as commonly understood by one of ordinary skill in the art to which this application belongs. The terminology used herein is for the purpose of describing particular embodiments only and is not intended to be limiting of any embodiment. Although specific methods and materials are described herein with respect to certain exemplary aspects of the present disclosure, it should be understood and appreciated that other methods and materials similar or equivalent to those described herein can be used in the practice or testing of the present application without straying from the intended scope of this disclosure.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should be further appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to effect such feature, structure, or characteristic in connection with other embodiments whether or not explicitly described.

Throughout this disclosure, various quantities, such as amounts, sizes, dimensions, proportions and the like, are presented in a range format. It should be understood that the description of a quantity in range format is merely for convenience and brevity and should not be construed as an inflexible limitation on the scope of any embodiment. Accordingly, the description of a range should be considered to have specifically disclosed all the possible subranges as well as all individual numerical values within that range unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 4.62, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise. Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "includes", "comprises", "including" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Additionally, it should be appreciated that items included in a list in the form of "at least one of A, B, and C" can mean (A); (B); (C); (A and B); (B and C); (A and C); or (A, B, and C). Similarly, items listed in the form of "at least one of A, B, or C" can mean (A); (B); (C); (A and B); (B and C); (A and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

The disclosed embodiments may, in some cases, be implemented in hardware, firmware, software, or a combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

The need for rapid diagnosis of disease states caused by infectious agents, such as viruses, has become of paramount importance since the worldwide outbreak of severe respiratory diseases caused by the novel coronavirus known as COVID-19. COVID-19 detection currently relies on testing for the virus, by reverse transcription polymerase chain reaction (RT-PCR), or viral proteins by antigen testing. However, COVID-19 causes significant metabolic changes in infected subjects due to both metabolic requirements for rapid viral replication and host immune responses. Volatile organic compounds (VOCs) of a disease are a diverse group of chemicals associated with metabolic pathways dysregulated in specific ways by the disease. Viruses themselves do not emit VOCs, but viruses indirectly cause emission of VOCs by inducing alteration, sometimes drastic alteration, in cellular metabolism. Viruses hijack metabolic resources for replication, and induce a mounted host body response. For example, SARS-CoV-2 is an enveloped virus, and therefore replication requires increased lipid/cholesterol metabolism. SARS-CoV-2 also binds to and depletes ACE2, which causes an upregulation of specific metabolites related to oxidative stress. Analysis of VOCs from human breath can detect these metabolic changes and is therefore an alternative to viral or antigen assays. Two of the major challenges in developing breath VOC sensors are: (1) a need to be highly sensitive because the concentrations of VOC biomarkers in exhaled breath are extremely low and (2) a need to be highly selective in detecting the target VOCs due to the presence of hundreds of gaseous components in breath, including water vapor.

In accordance with the present disclosure, sensor technologies, such as those utilizing nanoparticles and nanomaterials, can be combined with mobile communication devices, such as smart phones, and/or cloud computing to create technical solutions for rapid analysis and diagnosis of a COVID-19 Positive disease state. A nanoparticle sensor used in combination with the processor of a computing device, such as a smart phone and/or a remote server, and a biomarker processing module or engine with a neural network or pattern matching algorithm, can be used to detect VOCs exhaled by subjects in their breath. The detection and measurement of VOCs can be specifically correlated with COVID-19 infection. Real-time breath testing by simply exhaling into a device having such sensors, a computing device and biomarker processing module can provide particularly useful technical results, because the detection and measurement data can be immediately processed, e.g., by the smart phone or a remote processor via a cloud computing service and biomarker processing module or engine, and then real-time results can be made available to the subject or to a clinician, physician, or other professional, thus permitting relatively fast diagnoses and corresponding treatment decisions.

As used herein, "biomarker" refers to one or more signals and/or signal patterns associated with a presence of one or more substances, concentrations and/or amounts of respective substances associated with diagnosing a health condition or disease. In some instances, a biomarker can refer to one or more signals and/or signal patterns associated with a presence of a specific combination of substances at predefined concentrations and/or amounts.

As used herein, "real-time" refers to an event or a sequence of acts, such as those executed by a computer processor that are perceivable by a subject, person, user, or observer at substantially the same time that the event is occurring or that the acts are being performed. By way of example, if a neural network receives an input based on sensing and identifying an exhaled gas, a result can be generated at substantially the same time that the exhaled gas was sensed and identified. The real-time processing of the input by the neural network may have a slight time delay associated with converting the sensed exhaled gas to an electrical signal for an input to the neural network; however, any such delay may typically be less than 1 minute and usually no more than a few seconds.

In one aspect, the present disclosure provides methods for identifying VOCs that are present in the breath of a subject with a COVID-19 Positive disease state and/or for utilizing VOC sensor data to develop patterns or biosignatures representing a COVID-19 Positive disease state. In one embodiment, VOCs associated with a COVID-19 Positive disease state are identified and/or patterns or biosignatures representing a COVID-19 Positive disease state are developed using a SPME GC-MS QTOF method as described in the Examples herein below. In some embodiments, a biosignature may include, for example a VOC that is present in alveolar air exhaled by a subject having a COVID-19 Positive disease state but not present in alveolar air exhaled by a subject having a COVID-19 Negative disease state. In other embodiments, a biosignature may include a VOC that is present at a certain concentration, or at a certain concentration relative to another VOC, in alveolar air exhaled by a subject having a COVID-19 Positive disease state that is different from a concentration at which the VOC is present, or at a different concentration relative to another VOC, in alveolar air exhaled by a subject having a COVID-19 Negative disease state. In some embodiments, machine learning through forward feature selection and/or artificial neural networks is implemented on VOCs to develop a biosignature that exhibits improved diagnostic accuracy.

VOCs identified by SPME GC-MS QTOF inform the selection of sensing elements that are tailored for the biomarkers. This leads to fabrication of a nanosensor array that has high selectivity to the identified biomarkers and enable higher diagnostic accuracies relative to nonspecific gas sensor arrays. Each sensor is selected to respond to one or more specific VOC that correspond(s) to the COVID-19 Positive disease state, and/or one or more specific VOC that is/are present at concentrations correlating to a COVID-19 Positive disease state signature. The sensor also may, in some embodiments, demonstrate high sensitivity, selectivity, reproducibility, low degradation, and extended shelf life. While the present disclosure is not intended to be limited to specific sensor materials or specific sensor structures or architectures, a variety of suitable sensor materials, structures and architectures are known and are suitable for use in connection with the present disclosure. Examples include those that are described in U.S. patents and published patent applications owned by the present Applicant and by others including, for example and without limitation, U.S. Pat. No. 10,107,827 to Agarwal, et al., U.S. Patent Application Publication No. 2015/0295562 to Agarwal, et al., U.S. Patent Application Publication No. 2020/0337594 to Reddy and the patents, patent applications and nonpatent literature cited therein, all of which are hereby incorporated by reference herein in their entireties.

In another aspect of the present disclosure, there are provided methods for diagnosing a subject for a COVID-19 infection state. In one embodiment, the method includes (i) collecting an alveolar air breath sample from a subject; (ii) passing the breath sample into contact with a volatile organic compound (VOC) sensor operable to detect a plurality of VOC biomarkers for a COVID-19 infection state; (iii) producing a readable sensor output for at least two of the plurality of biomarkers; and (iv) diagnosing the COVID-19 infection state of the subject based on the readable sensor output. In one embodiment, the COVID-19 infection states (also referred to herein as "COVID-19 disease states") include COVID-19 Negative and COVID-19 Positive. In another embodiment, the COVID-19 infection states include COVID-19 Negative, COVID-19 Positive Symptomatic and COVID-19 Positive Asymptomatic.

In one embodiment, each of the plurality of VOC biomarkers is selected from the group consisting of an ester having a molecular weight of less than 200 g/mol, an aldehyde, and a terpene. As used herein, the term "terpene" is intended to include both terpenes and terpenoids. In one embodiment, the plurality of VOC biomarkers includes an ester having a molecular weight of less than 200 g/mol and at least one of an aldehyde and a terpene. Examples of esters having molecular weights of less than 200 g/mol that have been identified as VOC biomarkers of a COVID-19 Positive infection state include, for example, and without limitation, the esters set forth in Table 3 and isomers thereof. Examples of aldehydes that have been identified as VOC biomarkers of a COVID-19 Positive infection state include, for example, and without limitation, the aldehydes set forth in Table 3 and isomers thereof. Examples of terpenes that have been identified as VOC biomarkers of a COVID-19 Positive infection state include, for example, and without limitation, the terpenes set forth in Table 3 and isomers thereof. In one embodiment, each of the plurality of VOC biomarkers is selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; and Benzenemethanol, alpha-methyl-, acetate.

In other embodiments, the at least one VOC biomarker comprises at least two unsaturated terpenes, each having 5, 10 or 15 carbons, and at least one aldehyde. In still other embodiments, the at least one VOC biomarker comprises at least three VOCs wherein at least two of the VOCs are terpenes. In yet other embodiments, the at least one VOC biomarker comprises at least three VOCs wherein at least one of the VOCs is a terpene and at least one of the VOCs is an aldehyde or a ketone. In still yet other embodiments, the at least one VOC biomarker comprises at least three VOCs wherein at least one of the VOCs is an aldehyde and at least one of the VOCs is a ketone. In other embodiments, the at least one VOC biomarker comprises at least three VOCs wherein at least one of the VOCs is an aldehyde and at least one of the VOCs is an alcohol. In yet other embodiments, the at least one VOC biomarker comprises at least three VOCs wherein at least two of the VOCs are esters and at least one of the VOCs is a terpene. In certain embodiments, each of the esters, terpenes, aldehydes and ketones referenced in this paragraph is selected from the list of compounds set forth in the preceding paragraph. In other embodiments, the at least one VOC biomarker comprises at least three VOCs selected from the list of compounds set forth in the preceding paragraph. In another embodiment, the at least one VOC biomarker is selected from the group consisting of hexyl acetate (Acetic Acid, hexyl ester), 3.5.5-trimethyl-hexanal and alpha-cedrene. In other embodiments, the at least one VOC biomarker comprises at least two or at least three VOCs selected from the group consisting of hexyl acetate (Acetic Acid, hexyl ester), 3.5.5-trimethyl-hexanal and alpha-cedrene.

As indicated above, the readable sensor output in the method in one embodiment comprises a simple detection of a VOC that has been determined to be present in alveolar air exhaled by a subject having a COVID-19 Positive disease state but not by a subject having a COVID-19 Negative disease state. In another embodiment, the readable sensor output comprises a concentration measurement of a VOC that is present at a certain concentration, or at a certain concentration relative to another VOC, in alveolar air exhaled by a subject having a COVID-19 Positive disease state that is different from a concentration at which the VOC is present, or at a different concentration relative to another VOC, in alveolar air exhaled by a subject having a COVID-19 Negative disease state. In yet another embodiment, the readable sensor output comprises both simple detection data for at least one VOC that correlates to a COVID-19 infection state and concentration data for at least one VOC that correlates to a COVID-19 infection state.

In another embodiment, the method further includes: (v) determining a correlation between the readable sensor output and a predefined signal or signal pattern associated with the COVID-19 infection state; and (vi) identifying, based at least in part on the determination of a correlation with the predefined signal or signal pattern, the presence of the COVID-19 infection state. In yet another embodiment, the method further includes: (v) processing the readable sensor output via a neural network or pattern recognition algorithm, wherein the readable sensor output correlates with a predefined signal or signal pattern associated with the COVID-19 infection state; and (vi) identifying, based at least in part on the determination of a correlation with the predefined signal or signal pattern, the presence of the COVID-19 infection state. In still another embodiment, the method is accomplished by utilizing a VOC sensor that comprises (a) a first sensor component operable to expose one or more nanoparticles to at least one VOC in the alveolar air breath sample, wherein the one or more nanoparticles are operable to react to a presence of or contact with at least one of the plurality of VOC biomarkers; (b) a second sensor component operable to generate an electronic signal when the one or more nanoparticles react to the presence of or contact with the at least one of the plurality of VOC biomarkers, wherein the electronic signal is associated with a concentration or amount of the at least one of the plurality of VOC biomarkers; and (c) an electronic circuit operable to transmit the electronic signal to an output device or computer processor. In some embodiments, the sensor comprises an array of sensor subunits, each sensor subunit operable to detect at least one of the plurality of VOC biomarkers.

In yet another aspect, the present disclosure provides systems for detecting and identifying at least one VOC biomarker for a COVID-19 infection state in exhaled breath of a subject. In one embodiment, a system includes: (i) a mouth piece connected to a housing, the mouth piece operable to receive the exhaled breath of the subject; (ii) a sensor module disposed in the housing, the sensor module operable to detect the at least one VOC biomarker in the exhaled breath, and further operable to produce a readable sensor output for the at least one VOC biomarker; and (iii) a communication module disposed in the housing and in communication with the sensor module, the communication module operable to transmit collected data from the sensor module. In some embodiments, the sensor module comprises an array of sensor subunits, each sensor subunit operable to detect at least one of the plurality of VOC biomarkers.

In one embodiment, the sensor module comprises at least one array of sensor subunits, wherein each sensor subunit is operable to detect at least one VOC biomarker. In another embodiment, the COVID-19 infection state comprises a state selected from the group consisting of COVID-19 Negative and COVID-19 Positive. In yet another embodiment, the COVID-19 infection state comprises a state selected from the group consisting of COVID-19 Negative, COVID-19 Positive Symptomatic and COVID-19 Positive Asymptomatic. The at least one VOC biomarker can be selected in the same manner as described above with respect to the diagnosing methods described herein.

In one embodiment, the sensor module comprises at least one nanoparticle sensor. In another embodiment, the readable sensor output includes a concentration or amount for the at least one VOC biomarker. In yet another embodiment, the communication module is further operable to transmit collected data via at least one of the following: IR (infrared) communication, wireless communication, a Bluetooth protocol wireless communication, a direct wired connection, or to a remote processor or memory storage device.

In still another embodiment, the system further comprises a biomarker processing module in communication with the sensor module, the biomarker processing module operable to process the collected data associated with detection of the at least one VOC biomarker and to identify the at least one VOC biomarker. In some embodiments, the biomarker processing module is further operable to process the collected data via a neural network or pattern recognition algorithm, wherein a result from the biomarker processing module is received by the communication module for output to a software application loaded on a computer or a hand-held electronic device. In other embodiments, the biomarker processing module is further operable to process the collected data in conjunction with other sensor data, wherein a result from the biomarker processing module is received by the communication module for output to a software application loaded on a computer or a hand-held electronic device. In some embodiments, the software application is operable to communicate the collected data to a health care provider to facilitate tracking of the collected data.

It should be appreciated that the various methods and systems described herein may allow for the management of program elements/processes and communication of data to a health care provider or other repository of data. To enhance effectiveness of methods and systems described herein, the system in some embodiments includes a dynamic, mobile software application that can be used on smartphones and other mobile computing devices. Further, in some embodiments, landline and/or paper backups may be included in parallel processes. It should be appreciated that the software application loaded on a computer or a hand-held electronic device, can provide for standard as well as patient-specific adaptations to optimize a patient's engagement with the system as well as optimizing his or her medical condition and reporting back to the providers.

It should be appreciated that, in embodiments, the software application and associated system is HIPPA secure and cloud/server managed. In some embodiments, the application further supports download and capture into the EMR for documentation, quality and data management as well as supporting liability monitoring/documentation and proactive care modification. In some embodiments, a software application loaded on a computer or a hand-held electronic device, either a standard customize format, is executable to generate or provide a prompt for each action to be taken by a patient in accordance with a given diagnosis protocol.

It should be appreciated that the application may be embodied as any type of application suitable for performing the functions described herein. In particular, in some embodiments, the application may be embodied as a mobile application (e.g., a smartphone application), a cloud-based application, a web application, a thin-client application, and/or another type of application. For example, in some embodiments, an application may serve as a client-side interface (e.g., via a web browser) for a web-based application or service.

It should be further appreciated that the computing device executing the application may be embodied as any type of computing device capable of doing so. For example, in some embodiments, the computing device may be similar to the computing device 100 of FIG. 1. Referring now to FIG. 1, a simplified block diagram of at least one embodiment of a computing device 100 is shown. Depending on the particular embodiment, the computing device 100 may be embodied as a mobile computing device, cellular phone, smartphone, wearable computing device, personal digital assistant, desktop computer, laptop computer, tablet computer, notebook, netbook, Ultrabook™, Internet of Things (IoT) device, server, processing system, and/or any other computing, processing, and/or communication device capable of performing the functions described herein.

The computing device 100 includes a processing device 102 that executes algorithms and/or processes data in accordance with operating logic 108, an input/output device 104 that enables communication between the computing device 100 and one or more external devices 210, and memory 106 which stores, for example, data received from the external device 210 via the input/output device 104.

The input/output device 104 allows the computing device 100 to communicate with the external device 110. For example, the input/output device 104 may include a transceiver, a network adapter, a network card, an interface, one or more communication ports (e.g., a USB port, serial port, parallel port, an analog port, a digital port, VGA, DVI, HDMI, FireWire, CAT 5, or any other type of communication port or interface), and/or other communication circuitry. Communication circuitry of the computing device 100 may be configured to use any one or more communication technologies (e.g., wireless or wired communications) and associated protocols (e.g., Ethernet, Bluetooth®, Wi-Fi®, WiMAX, etc.) to bring about such communication depending on the particular computing device 100. The input/output device 104 may include hardware, software, and/or firmware suitable for performing the techniques described herein.

The external device 110 may be any type of device that allows data to be inputted or outputted from the computing device 100. For example, in various embodiments, the external device 110 may be embodied as a server (e.g., a cloud-based server). Further, in some embodiments, the external device 110 may be embodied as another computing device, switch, diagnostic tool, controller, printer, display, alarm, peripheral device (e.g., keyboard, mouse, touch screen display, etc.), and/or any other computing, processing, and/or communication device capable of performing the functions described herein. Furthermore, in some embodiments, it should be appreciated that the external device 110 may be integrated into the computing device 100.

The processing device 102 may be embodied as any type of processor(s) capable of performing the functions described herein. In particular, the processing device 102 may be embodied as one or more single or multi-core processors, microcontrollers, or other processor or processing/controlling circuits. For example, in some embodiments, the processing device 102 may include or be embodied as an arithmetic logic unit (ALU), central processing unit (CPU), digital signal processor (DSP), and/or another suitable processor(s). The processing device 102 may be a programmable type, a dedicated hardwired state machine, or a combination thereof. Processing devices 102 with multiple processing units may utilize distributed, pipelined, and/or parallel processing in various embodiments. Further, the processing device 102 may be dedicated to performance of just the operations described herein, or may be utilized in one or more additional applications. In the illustrative embodiment, the processing device 102 is programmable and executes algorithms and/or processes data in accordance with operating logic 108 as defined by programming instructions (such as software or firmware) stored in memory 106. Additionally or alternatively, the operating logic 108 for processing device 102 may be at least partially defined by hardwired logic or other hardware. Further, the processing device 102 may include one or more components of any type suitable to process the signals received from input/output device 104 or from other components or devices and to provide desired output signals. Such components may include digital circuitry, analog circuitry, or a combination thereof.

The memory 106 may be of one or more types of non-transitory computer-readable media, such as a solid-state memory, electromagnetic memory, optical memory, or a combination thereof. Furthermore, the memory 106 may be volatile and/or nonvolatile and, in some embodiments, some or all of the memory 106 may be of a portable type, such as a disk, tape, memory stick, cartridge, and/or other suitable portable memory. In operation, the memory 106 may store various data and software used during operation of the computing device 100 such as operating systems, applications, programs, libraries, and drivers. It should be appreciated that the memory 106 may store data that is manipulated by the operating logic 108 of processing device 102, such as, for example, data representative of signals received from and/or sent to the input/output device 104 in addition to or in lieu of storing programming instructions defining operating logic 108. As shown in FIG. 1, the memory 106 may be included with the processing device 102 and/or coupled to the processing device 102 depending on the particular embodiment. For example, in some embodiments, the processing device 102, the memory 106, and/or other components of the computing device 100 may form a portion of a system-on-a-chip (SoC) and be incorporated on a single integrated circuit chip.

In some embodiments, various components of the computing device 100 (e.g., the processing device 102 and the memory 106) may be communicatively coupled via an input/output subsystem, which may be embodied as circuitry and/or components to facilitate input/output operations with the processing device 102, the memory 106, and other components of the computing device 100. For example, the input/output subsystem may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations.

The computing device 100 may include other or additional components, such as those commonly found in a typical computing device (e.g., various input/output devices and/or other components), in other embodiments. It should be further appreciated that one or more of the components of the computing device 100 described herein may be distributed across multiple computing devices. In other words, the techniques described herein may be employed by a computing system that includes one or more computing devices. Additionally, although only a single processing device 102, I/O device 104, and memory 106 are illustratively shown in FIG. 1, it should be appreciated that a particular computing device 100 may include multiple processing devices 102, I/O devices 104, and/or memories 106 in other embodiments. Further, in some embodiments, more than one external device 110 may be in communication with the computing device 100.

EXAMPLES

The following examples are given for the purpose of illustrating various embodiments of the invention and are not meant to limit the present invention in any fashion. The present examples, along with the methods described herein are presently representative of embodiments, are provided only as examples, and are not intended as limitations on the scope of the invention. Changes therein and other uses which are encompassed within the spirit of the invention as defined by the scope of the claims will occur to those skilled in the art.

Example 1

Introduction

Viruses themselves do not emit VOCs. However, viruses induce dramatic alteration in cellular metabolism through two mechanisms: hijacking metabolic resources for viral replication, and the mounted host body response. Because SARS-CoV-2 is an enveloped virus, replication requires increased lipid, including cholesterol metabolism[16]. An example of host body response is that SARS-CoV-2 binds to angiotensin-converting enzyme 2 (ACE2) for cell entrance, but also depletes ACE2[17] which blocks the antioxidant response and thereby causes an upregulation of metabolites related to oxidative stress[18, 19]. In addition, the metabolic response to any viral infection is unique to each particular virus: previous researchers have identified specific VOC patterns that are associated with three influenza viruses, respiratory syncytial virus and rhinovirus[20]. Similarly, a VOC signature can be determined and utilized specifically for noninvasive COVID-19 diagnostic purposes.

Headspace solid phase microextraction coupled with gas chromatography-mass spectrometry quadrupole time-of-flight (HS-SPME GC-MS QTOF) were used to analyze VOCs associated with COVID-19 infection states in largely young, healthy COVID-19 subjects and COVID-19 negative controls. By use of this sensitive technique, the current study sought to increase knowledge of metabolic changes caused by COVID-19 as evidenced by changes in functional groups of detected VOCs. More specifically, to identify VOC biomarkers of COVID-19, alveolar breath samples were collected from two sample groups into Tedlar bags: negative COVID-19 (n=12) and positive COVID-19 symptomatic (n=14). Next, VOCs were analyzed by headspace solid phase microextraction coupled to gas chromatography-mass spectrometry (HS-SPME GC-MS). Subjects with COVID-19 displayed a larger number of VOCs as well as overall higher total concentration of VOCs (p-value<0.05). Univariate analyses of qualified endogenous VOCs (ranksum) showed approximately 18% of the VOCs were significantly differentially expressed between the two classes (p<0.05), with most upregulated. Machine learning multivariate classification algorithms distinguished COVID-19 subjects with over 95% classification accuracy. The COVID-19 positive subjects could be differentiated into two distinct subgroups by machine learning classification, but these did not correspond with significant differences in number of symptoms. Next, samples were collected from subjects who had previously donated breath bags while experiencing COVID-19, and subsequently recovered (COVID Recovered subjects (n=11)). Univariate and multivariate results showed>90% accuracy at identifying these new samples as Control (COVID-19 negative), thereby validating the developed classification algorithms.

Materials and Methods

Materials and Instrumentation

Reagent alcohol, Parafilm, and ViroMax filters were purchased from Fisher Scientific USA (Florence, KY). A Pressure Controller (flowmeter) was purchased from Alicat (Tucson, AZ). 20 mL headspace vials with screw cap lids, deactivated glass wool, 3 L Tedlar gas sampling bags, and one cm polydimethylsiloxane/carboxen/divinylbenzene (PDMS/CAR/DVB) SPME fibers were manufactured and purchased from Restek (Bellefonte, PA). VOCs sampled and concentrated by the SPME fiber were analyzed using an Agilent (Santa Clara, CA) 7890A GC system coupled to an Agilent 7200 accurate-mass QTOF MS system with a PAL autosampling system (CTC Analytics; Raleigh, NC). The column utilized was an Agilent HP-5 ms, 5% phenyl methyl siloxane GC column of 30 m length, 250 μm internal diameter, and 0.25 μm film thickness.

Patient Recruitment

Institutional Review Board (2008193976) and Biosafety Committee (IN—1301) permissions from Indiana University were obtained. Subjects were recruited and included persons who received RT-PCR tests through IU Health because they were symptomatic, in close contact with persons who were symptomatic, or were scheduled for mitigation testing. Exclusion criteria included persons currently experiencing an unstable or serious underlying medical condition, under fourteen years of age or who did not feel comfortable blowing into a Tedlar bag. At the time of consent, the subjects were instructed on how to provide an appropriate breath sample into the 3 L Tedlar bag and queried as to whether they were currently experiencing the following eight symptoms (fever, diarrhea, shortness of breath, sore throat, dry cough, loss of taste/smell, chills or body aches, and headache/tiredness). Subjects were also provided with an instructional video containing details on how to properly fill the Tedlar bag with exhaled breath. A time was scheduled with each subject for the researcher(s) to deliver a kit including all the materials required for sample collection. After filling the bag, the subjects answered questions again about their current symptoms and placed the kit with the bag outside of their homes, and the kit was transported back to Indiana University—Purdue University (IUPUI) for chemometric analysis.

Exhaled Breath Sampling

Breath samples were collected into 3 L Tedlar bags modifying a procedure which has been previously published and shown to be effective in collecting exhaled breath with relative increased amounts of carbon dioxide[13]. Briefly, subjects held their breath and then blew through a ViroMax viral filter (viral filtration efficiency greater than 99.99%) coupled to a Tedlar bag through a small opening, until the bag was approximately 75-80% full. Next, subjects placed the bags in secondary polypropylene bags which were sanitized with reagent alcohol (70%) prior to transportation back to the facility. All Tedlar bags containing the breath samples were visually inspected to ensure each of the breath samples were collected correctly. Previous breath collections (prior to the COVID-19 pandemic) did not include use of a viral filter or addition of a secondary container that could be wiped down with reagent alcohol. Therefore, the modified protocol was compared with the previously implemented protocol quantitatively, to ensure the safety modifications did not impede the detection of VOCs in exhaled breath samples. Next, breath samples were collected from subjects who were diagnosed COVID-19 negative (Control), and COVID-19 positive (COVID-19). Additionally, samples were collected from COVID-19 positive subjects more than 60 days after their initial diagnosis (COVID Recovered).

Sample Processing and Storage

Within 24 hours of collection, VOCs were cryotransferred to a precleaned 20 mL headspace vial containing deactivated glass wool using a previously described protocol[13]. In short, the headspace vial cap septa were pierced by two stainless steel needles, one long and one short, to enable gas flow through the headspace vials. The cryotransfer method entailed cooling the samples to −45° C. and then using a vacuum with the pressure controller (flowmeter) to pull the air slowly and consistently from the Tedlar bags, depositing the VOCs onto the glass wool and the inner glass walls of the headspace vial. The headspace vials were wrapped with parafilm and stored at −80° C. and analyzed by HS-SPME GC-MS QTOF. The rationale for cryotransfer is that it allows for longer term storage VOCs at −80° C., as VOCs collected in Tedlar bags are not stable for storage[26]. In turn, this also enables the GC-MS analysis of samples over a relatively shorter period of time, thereby decreasing the amount of instrumental drift observed over the course of the study.

HS-SPME GC-MS QTOF Analysis

Figure 2:
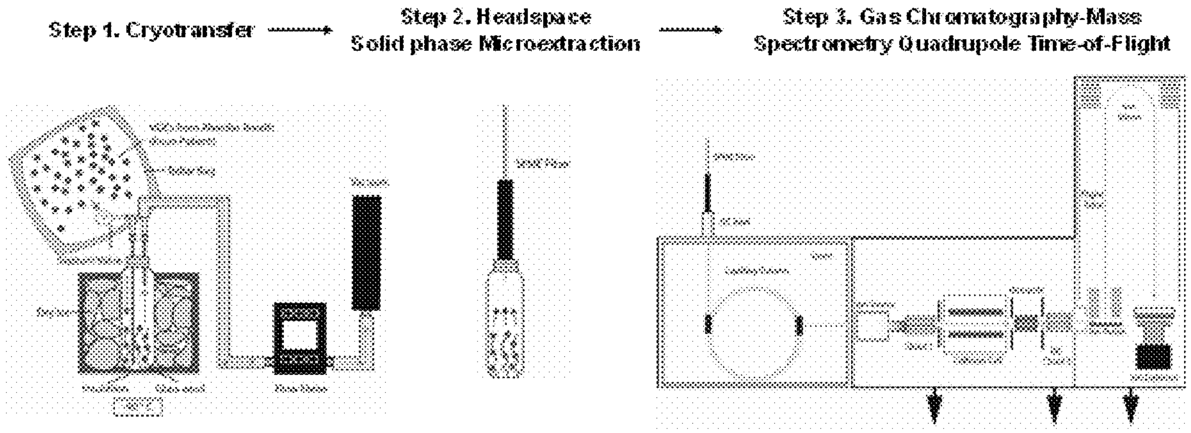
FIG. 2 is an illustration of cryotransferring VOCs collected in a Tedlar bag to a 10 mL headspace vial, headspace solid phase microextraction to concentrate the analytes and GC-MS QTOF to separate, quantify and structurally elucidate biomarkers of COVID-19. Note: a viral filter (not shown) was interfaced between the flow meter and the vacuum for biosafety precautions.

PDMS/CAR/DVB SPME fibers were conditioned at 250° C. for 10 min prior to the first run every day and for 4 minutes between runs. Samples were warmed to room temperature before analysis. Next, samples were agitated at 250 rpm and 60° C. while the SPME fiber was incubated in the sample headspace for 45 minutes. After extraction, the SPME fiber was inserted into the GC inlet at 250° C. for 2 min to thermally desorb the VOCs. The oven temperature was increased from 40° C. to 260° C. using a 5° C./min linear ramp. The MS transfer line was held at 250° C. Analytical reference standards were analyzed daily and demonstrated reproducible measurements over the course of the experiment. The GC-MS signals for the reference standards during the experiment displayed a relative standard deviation equal to 5.6%. An illustration of cryotransfer, HS-SPME and GC-MS QTOF analysis can be observed in FIG. 2.

Data Processing, Chemometric Analyses, and Validation Study

HS-SPME GC-MS QTOF data were collected in centroid format and the sample chromatograms were spectrally aligned in MassHunter Profinder to identify conserved VOCs. Molecular features identified as silanes/siloxanes and VOCs not detected in at least half of one sample class (Control or COVID-19) were disqualified from further chemometric analysis. The Mann-Whitney U univariate (nonparametric) significance test was employed to observe differences in VOC concentrations (p-value<0.05). For multivariate analyses, signals were autoscaled (z-scored) by VOC. Multivariate analysis (including hierarchical clustering, principal component analysis (PCA), linear discriminant analysis (LDA) and others) were employed to observe patterns in the data and build a predictive classification model. Ellipses shown in the PCA plots were made by the authors for visual reference only. More than 60 days after collection of initial samples, the subjects that were COVID-19 positive were contacted and requested to furnish a second sample (COVID Recovered). These samples may be considered a validation cohort. Lastly, the output from the multivariate models of VOCs identified as differentially expressed due to COVID-19 were analyzed for significant differences due to confounding variables age (using linear regression analysis) and sex (using the Mann-Whitney U-test).

Results

Modification of Method for COVID-19 and Patient Recruitment/Sample Collection

Prior to commencing wider collection, breath samples were collected from a single consented subject using two methods: the previous method involving Tedlar bag collection[13] and the method including breathing first through a viral filter into the Tedlar bag and next placing the bag in a secondary container disinfected with alcohol. Samples of each type were collected, cryotransferred, and analyzed by GC-MS QTOF to determine whether use of filter and disinfection impeded the detection of VOCs. There was no statistically significant difference in the total number of VOCs detected or the total integrated signal between the previous method and the modified, COVID-19 method (relative standard deviation (RSD) of the total signal was equal to 9.9%). No increases in isopropanol, methanol or ethanol (reagent alcohol used to wipe off outer bag) were observed when utilizing the modified procedure. Once the collection procedure was shown to not impede the sampling or analysis of VOCs, breath samples were collected from Control (n=12) and COVID-19 symptomatic subjects (n=14). VOC analysis subsequently suggested this cohort be segregated into two groups, COVID-1 and COVID-2, as will be discussed below. Additionally, COVID-19 Recovered samples (n=11) were collected from subjects in the COVID-19 cohort at least two months after their initial diagnosis. A list of all subjects' age, gender, reason for receiving a COVID-19 test and number of symptoms at consent and at breath collection are set forth in Table 1, which is summarized in Table 2. All of the subjects consented in this study were not experiencing serious co-existing medical conditions, and there were only two smokers in the study (both belonging to the COVID-19 Negative sample class).

TABLE 1

Age, gender, and reason for receiving a diagnostic test for COVID-19 for all of the subjects included in the study. COVID-19 positive subjects were divided into a COVID 1 subgroup, shown in italics below, and a COVID 2 subgroup, shown in bold below.

| Test | Age | Gender | Reason for Testing | # Reported Symptoms At Consent | At Collection |
|---|---|---|---|---|---|
| COVID-19 Negative | 28 | F | Close Contact | 4 | 4 |
| | 25 | M | Close Contact | 0 | 0 |
| | 25 | M | Close Contact | 2 | 2 |
| | 23 | F | Close Contact | 0 | 0 |
| | 25 | F | Close Contact | 0 | 0 |
| | 34 | M | Close Contact | 1 | 0 |
| | 27 | M | Close Contact | 0 | 0 |
| | 25 | F | Close Contact | 0 | 0 |
| | 23 | M | Mitigation | 0 | 0 |
| | 26 | F | Mitigation | 0 | 0 |
| | 23 | F | Mitigation | 0 | 0 |
| | 57 | F | Mitigation | 0 | 0 |
| COVID-19 Positive | **25*** | **M** | **Close Contact** | **3** | **0** |
| | *24** | *F* | *Close Contact* | *6* | *4* |
| | **30** | **M** | **Close Contact** | **3** | **2** |
| | **26*** | **M** | **Close Contact** | **4** | **4** |
| | *32** | *M* | *Close Contact* | *3* | *3* |
| | **27*** | **M** | **Close Contact** | **3** | **2** |
| | *26** | *M* | *Close Contact* | *3* | *3* |
| | *26* | *F* | *Close Contact* | *3* | *3* |
| | **38*** | **M** | **Close Contact** | **7** | **7** |
| | *24** | *M* | *Close Contact* | *3* | *3* |
| | *28* | *M* | *Close Contact* | *3* | *3* |
| | **25*** | **F** | **Close Contact** | **6** | **6** |
| | **24*** | **M** | **Close Contact** | **6** | **6** |
| | **37*** | **F** | **Close Contact** | **6** | **6** |

*These COVID-19 subjects donated samples two months after diagnosis and reported no symptoms at time of second breath donation (COVID Recovered).

TABLE 2

Subject Info Summarized

| Test Result[1] | Number of Samples | Age Range (y/o) | Gender[2] | Reason of Testing[3] | Avg. Reported Symptoms Consent | Collection |
|---|---|---|---|---|---|---|
| Control | 12 | 23-57 | 7 - F<br>5 - M | 8 - CC<br>4 - Mit. | 0.6 ± 1.2 | 0.5 ± 1.2 |
| C-19+ (COVID 1) | 6 | 24-32 | 2 - F<br>4 - M | 6 - CC | 3.5 ± 1.2 | 3.2 ± 0.4 |
| C-19+ (COVID 2) | 8 | 24-38 | 2 - F<br>6 - M | 8 - CC | 4.7 ± 1.7 | 4.1 ± 2.5 |
| C-19+ Recovered | 11 | 24-38 | 3 - F<br>8 - M | 11 - CC | 0 | 0 |

[1]C-19+ = Covid-19 Positive;
[2]F = female, M = male;
[3]CC = close contact, Mit. = mitigation.

Data Screening and Univariate Chemometrics

Spectral alignment identified 341 deconvoluted VOCs detected in the 26 samples. After removing silanes/siloxanes (thermal degradation products of SPME and GC) and molecular features not detected in at least 50% of one or the other sample class (Control or COVID-19), 221 VOCs remained for further chemometric analyses. The sum of signals from these 221 VOCs comprises the total useful signal (TUS) for each sample. No sample outliers were identified when analyzing the TUS or the number of VOCs detected. Interestingly, TUS for the COVID-19 group was statistically significantly higher than the control group (p-value<0.05) (FIG. 3(*a*)). After observing that COVID-19 samples had significantly higher TUS, it was decided not to normalize the data by relative abundance. Utilizing relative abundance is only appropriate if the differences in total signal are not related to disease diagnosis. Additionally, the number of different VOCs identified was also larger in the COVID-19 group (p-value<0.01) (FIG. 3(*b*)), suggesting presence of COVID activates otherwise dormant or inactive metabolic pathways. Next, the Mann-Whitney U test was run, comparing VOCs from subjects with and without COVID-19. This test identified a remarkable 41 molecular features (~18% of 221) with p<0.05. These 41 VOCs are identified in Table 3, except for one VOC which was not found in the database and therefore was not identified.

TABLE 3

List of VOCs detected in alveolar breath with high potential to discriminate COVID-19. VOCs bolded are utilized for LDA classification.

| VOC# | Name | RT | p-value | $log_2FC$ |
|---|---|---|---|---|
| **1** | **Acetic Acid, hexyl ester (hexyl acetate)** | **10.78** | **3.90E−04** | **3.72** |
| **2** | **Hexanal, 3.5.5-trimethyl-** | **9.43** | **1.19E−03** | **3.31** |
| 3 | o-Cymene | 11.04 | 1.30E−03 | 1.63 |
| 4 | Eucalyptol | 11.26 | 2.21E−03 | 2.38 |
| 5 | 3,5,5-Trimethylhexyl acetate | 15.53 | 2.75E−03 | 4.48 |
| 6 | Bicyclo[2.2.1] heptan-2-ol, 1,3,3-trimethyl-, acetate, (1S-exo)- | 16.87 | 2.81E−03 | 3.10 |
| 7 | Cyclohexane, 2-butyl-1,1,3-trimethyl- | 16.73 | 2.81E−03 | 3.65 |
| 8 | Linalool | 13.35 | 3.05E−03 | 1.67 |
| 9 | 1-Decanol, 2-ethyl- | 19.47 | 4.61E−03 | 2.12 |
| 10 | α-Bisabolene | 21.54 | 4.87E−03 | 1.43 |
| 11 | 2-Octanone | 10.13 | 5.24E−03 | 1.48 |
| **12** | **α-Cedrene** | **22.07** | **5.90E−03** | **2.30** |
| 13 | 5-Heptenal, 2,6-dimethyl- | 10.43 | 5.93E−03 | 0.71 |
| 14 | Unidentified VOC 1 | 16.95 | 6.29E−03 | 2.38 |
| 15 | β-Bourbonene | 19.98 | 7.82E−03 | 3.00 |
| 16 | α-Phellandrene | 10.59 | 8.40E−03 | 2.06 |
| 17 | Nonane, 2,2,4,4,6,8,8-hepfamethyl- | 20.8 | 1.06E−02 | 2.77 |
| 18 | Dihydromyrcenol | 12.51 | 1.06E−02 | 1.84 |
| 19 | 3-Thujene | 8.27 | 1.45E−02 | 1.76 |
| 20 | Terpinene | 12.09 | 1.46E−02 | 1.80 |
| 21 | Hexane, 3,4-bis(1,1-dimethylethyl)-2,2,5,5-tetramethyl- | 20.74 | 1.46E−02 | 0.51 |
| 22 | Benzene, 1,3-dichloro- | 10.62 | 1.72E−02 | 1.71 |
| 23 | Hexane, 1-(hexyloxy)-5-methyl- | 19.67 | 1.81E−02 | 3.92 |
| 24 | Nonane, 3,7-dimethyl- | 11.49 | 1.87E−02 | 2.17 |
| 25 | D-Limonene | 11.16 | 1.93E−02 | 0.45 |
| 26 | Camphor | 14.66 | 1.94E−02 | 3.24 |
| 27 | Dodecane, 2,7,10-trimethyl- | 20.48 | 2.13E−02 | 1.90 |
| 28 | Hexadecane | 26.51 | 2.21E−02 | 0.65 |
| 29 | 4-tert-Butylcyclohexyl acetate | 18.91 | 2.34E−02 | 1.42 |
| 30 | 3-Undecene, 5-methyl- | 16.04 | 2.53E−02 | 0.33 |
| 31 | α-Terpinyl acetate | 20.4 | 2.80E−02 | 1.73 |
| 32 | 3-carene | 11.78 | 2.93E−02 | 1.74 |
| 33 | 1-Menthone | 14.94 | 3.28E−02 | −0.71 |
| 34 | Copaene | 21.12 | 3.72E−02 | 0.66 |
| 35 | Undecane, 2,3-dimethyl- | 18.06 | 4.22E−02 | 0.40 |
| 36 | Diethyl Phthalate | 26.44 | 4.22E−02 | 1.16 |
| 37 | Terpinen-4-ol | 15.63 | 4.32E−02 | 0.80 |
| 38 | Toluene | 4 | 4.48E−02 | −1.51 |
| 39 | 2-Undecene, 9-methyl- | 15.86 | 4.69E−02 | 0.78 |
| 40 | Caryophyllene | 22.25 | 4.77E−02 | 0.89 |
| 41 | Benzenemethanol, .alpha.-methyl-, acetate | 16.14 | 4.92E−02 | 1.58 |

Figure 3:
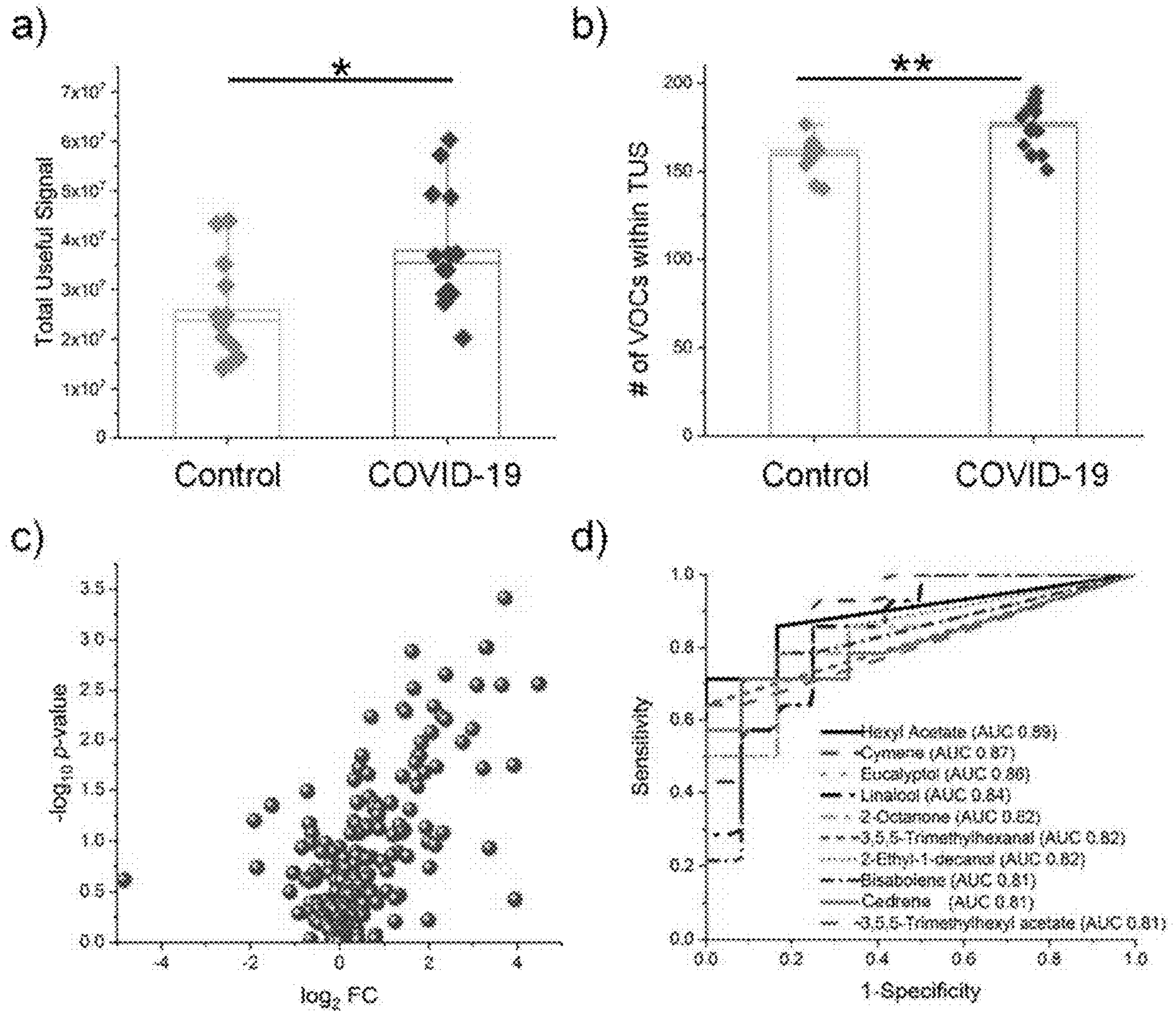
FIG. 3 depicts an overlapped bar chart showing COVID-19 group has higher (a) total VOC signal and (b) total number of molecular features after data screening (MS-TUS). (c) Volcano plot interpolating statistical significance as a function of fold change COVID-19 and Control Groups. (d) Receiver operator characteristic (ROC) curves for the top 10 individual VOCs that discriminate COVID-19 (AUCs range from 0.89 to 0.81). Statistical significance by the Wilcoxon Ranksum test is denoted by $*p<0.05$ and $**p<0.01$.

$Log_2$ Fold Change (FC) values versus $-Log_{10}$ p values for all 221 VOCs (volcano plot) are shown in FIG. 3(*c*). This plot indicates that most potential biomarkers are upregulated in the COVID-19 group. This result is expected as the TUS and number of individual VOCs were also elevated in the same group. Next, individual VOCs were analyzed for their ability to distinguish COVID-19 and the receiver operator characteristic (ROC) curves for the top ten VOCs are shown in FIG. 3(*d*)). Each of the ten VOCs have ROC area under the curve (ROC AUC) values >0.80, which is remarkably high for individual VOCs.

COVID-19 VOC Heterogeneity

A heatmap which clusters the data by VOC signal similarity was generated, and it was observed the COVID-19 subjects had relatively higher intraclass variation. This suggested utilizing hierarchical clustering of the COVID-19 samples themselves (FIG. 4(*a*)). Visually, the COVID-19 sample class separates into two subclasses (COVID 1 and COVID 2). These subclasses suggest dividing the VOCs themselves into three sections (top, middle, and bottom) based on differences in expression among the Control, COVID 1 and COVID 2 groups. The COVID 1 subgroup displays relatively low signals for many VOCs when compared to COVID 2, particularly in the middle section, but also to some degree in the top section. The 41 VOCs depicted by number (and functional group) in the heatmap are identified in Table 3. There are interesting differences between the COVID 1 group and the COVID 2 group analyzed as a whole. Initially, it is noted that the TUS for the COVID 2 group is much higher than for the COVID 1 group ($p<0.01$). Moreover, the COVID 2 group samples contain statistically significantly more VOCs than the COVID 1 group samples, both in the full set of 221 VOCs and in the smaller set of VOCs in Table 3 and shown on the heatmap. Four VOCs are present in the COVID 2 samples in significantly higher concentrations than in either the COVID 1 or Control samples. As discussed below, all four of these VOCs are esters.

The possibility that the presence of two COVID-19 subgroups may be due to the number of symptoms a subject reported (as a proxy for COVID-19 severity) was explored next. The average self-reported number of symptoms are listed in Table 1 for two time points: time of consent, and time of breath collection. Using single tailed tests (as COVID 2 group expected to have more symptoms), the Mann-Whitney U test did not demonstrate statistical significance at the time of consent but had a relatively low p-value (equal to 0.08). Symptoms at the time of sample collection were also not significant and had a higher p-value (equal to 0.26). Number of days since the first COVID-19 associated symptom was not collected.

Multivariate Classification

First, unsupervised PCA was implemented on the VOCs with $p<0.05$. Not only was there good separation between Control and COVID-19, but the COVID 1 and COVID 2 subgroups are completely separated (FIG. 4(*b*)). Across the first two principal components, 39% of the sample variance is accounted for and control samples are separated from both COVID 1 and COVID 2 subgroups with 96% overall accuracy (FIG. 4(*b*)). It can be noted that when utilizing 16 VOCs (those with p-value<0.01), all three sample groups are distinguished with 100% accuracy (FIG. 4(*d*)). Next, PCA was implemented to visualize differences between VOC functionality for the 41 molecular features identified with p-value<0.05 (FIG. 4(*c*)). The first two principal components account for approximately 30% of the VOC variance, and interestingly, terpenes/terpenoids cluster with aldehydes/ketones and are well distinguished from esters (one terpene/terpenoid clustered with the esters and one ester was grouped with the terpenes/terpenoids). Alkanes also clustered with esters. A similar result (but accounting for nearly 50% of variance) was obtained when utilizing PCA to visualize the 16 VOCs with p-value<0.01 (FIG. 4(*e*)). These analyses show that the VOC functional groups have different signatures within this sample cohort.

Figure 4:
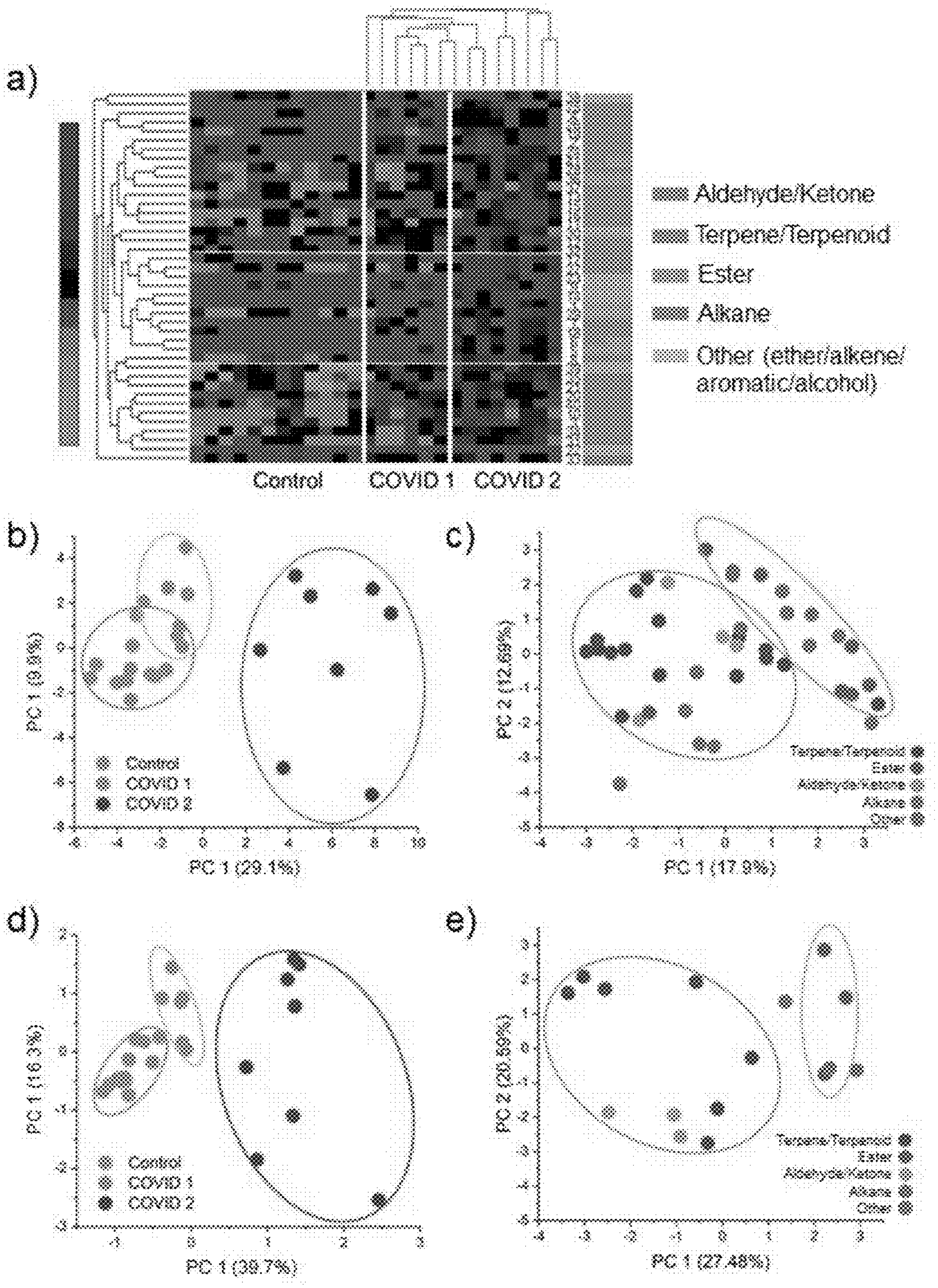
FIG. 4 sets forth the following: (a) Hierarchical clustergram showing COVID-19 subjects cluster into two groups (COVID 1 and COVID 2). COVID 1 has lower VOC signals relative to COVID 2, especially in the middle section. VOC numbers correspond to numbers in Table 3. Functional groups are shown at right. (b) PCA of top 41 VOCs ($p<0.05$) shows COVID 1 and COVID 2 separate. (c) Reverse PCA plotting the 41 VOCs show esters and alkanes in one cluster and terpenes and ketones/aldehydes in a separate cluster. (d) PCA of top 16 VOCs ($p<0.01$) separates Control, COVID 1 and COVID 2 with 100% accuracy. (e) PCA plot of top 16 VOCs shows same functional group separations as top 41 VOCs.
Figure 5:
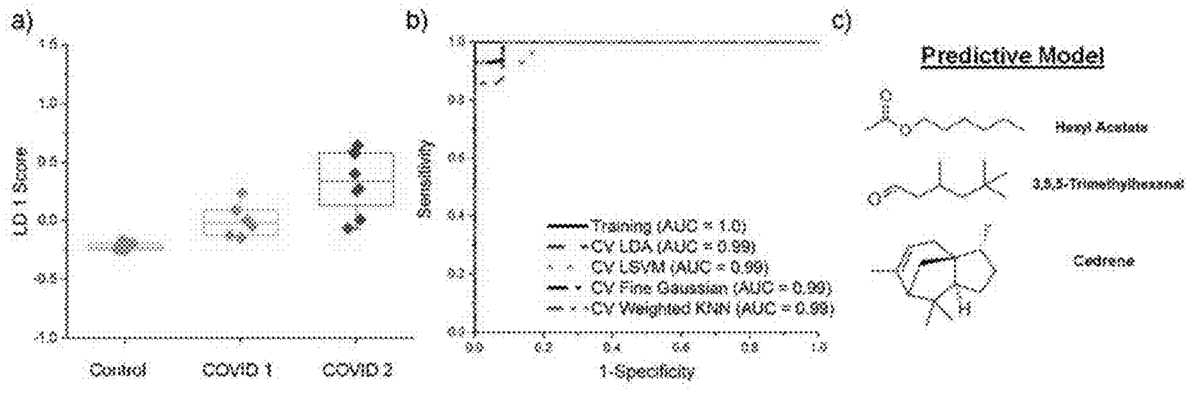
FIG. 5 sets forth the following: (a) Linear discriminant analysis one dimensional plot showing both COVID 1 and COVID 2 samples are perfectly distinguished from Control, but not from each other. (b) The associated ROC curves for LDA training and LDA five-fold cross validation (CV). Additional classifiers yield the same CV result and include linear support vector machine (LSVM), fine gaussian SVM, and weighted k-nearest neighbors (KNN). (c) Chemical structures of the three VOCs utilized in the LDA classification model.

The PCA models shown in FIGS. 4(*b*) and (*d*) utilized a high number of VOCs. To limit the number of VOCs used and to create a predictive classification model, forward feature selection coupled to LDA[9, 13, 27] was employed. A panel of three VOCs were identified which could distinguish COVID-19 subjects with 100% diagnostic accuracy in the training data set (furthermore, both subgroups, COVID 1 and COVID 2 were also distinguished with high accuracy). One dimensional LDA box and whisker plots for the training data can be observed in FIG. 5(*a*). To ensure the model is not overfit, fivefold cross validation was undertaken (1,000×). The ROC for the median cross-validated result is presented in FIG. 5(*b*) which shows an ROC AUC of 0.99, sensitivity=100% and specificity=92%. Furthermore, the model was functionally perturbed by presenting results using the same molecular features and different classification models (linear support vector machine (LSVM), Fine Gaussian SVM and Weighted K-Nearest Neighbors (KNN)). These ROC curves, even after cross-validation, produced AUC values equal to 0.99, indicating this biosignature of these three VOCs can accurately and robustly detect COVID-19 (FIG. 5(*b*)). The LDA panel of three VOCs contains hexyl acetate, cedrene and 3,5,5-trimethylhexanal (an ester, a terpene and an aldehyde). Table 3 and FIG. 5(*c*). These three VOC identities have been verified by running pure analytical standards by GC-MS. Further explanation on the biological relevance of these VOC biomarkers in the context of COVID-19 diagnosis is provided in the Discussion. Finally, outputs from both PCA models and the LDA model showed no significant differences due to biological sex and no significant correlations with subject age.

Analyzing COVID-19 Recovered Samples as a Validation Cohort

The COVID-19 recovered samples collected more than two months after original collection were evaluated in terms of univariate significance (regarding the 41 VOCs initially identified to be dysregulated by COVID-19) and multivariate classification (using the previously developed panels of VOCs for PCA and LDA). A heatmap of the 41 VOCs in the four sample classes (Control, COVID 1, COVID 2 and COVID Recovered) can be observed in FIG. 6(*a*) and shows many of the VOCs are restored to baseline levels after COVID-19 subjects have recovered. Specifically, 34 of the 41 VOCs had $p<0.05$ between the COVID-19 group and COVID Recovered. In addition, only 5/41 VOCs were still upregulated between COVID Recovered and Control. When utilizing the previously described PCA assays for separation, COVID Recovered samples are distinguished from the COVID-19 samples with over 90% specificity (FIG. 6(*b*-*c*)). Lastly, the LDA model initially presented in FIG. 5 was used to test the COVID Recovered samples (FIG. 6(*d*)). For the most part, COVID Recovered samples clustered with Control samples, and COVID-19 samples were distinguished from COVID Recovered samples with over 90% accuracy (one COVID Recovered sample error). This demonstrates the validation cohort of recovered subjects showed similar accuracy as the statistical cross-validation.

Discussion

The sampling and storage method for this study used a modified procedure that has been previously utilized for hypoglycemia VOC biomarker discovery in breath[13]. The modifications include utilizing a viral filter and sanitizing a secondary container with the Tedlar bag using reagent alcohol, which was shown to not impede the detection of VOCs. Additionally, even though breath samples were collected by the patient themselves in an unsupervised fashion in their homes, subjects were provided detailed instructions on breath sample collection by telephone and an instructional video. All breath samples were inspected after collection to ensure the Tedlar bags were filled adequately. The sample classes presented in Table 2 show that the COVID-19 samples had more males, and the Control samples had more female subjects. However, the VOCs implicated as biomarkers for COVID-19 did not show significant differences due to biological sex. In addition, the 12 Control subjects had a different age range relative to the other sample classes. This was due to the collection of a breath sample from a single subject who was 57 years of age. The age range of the other 11 Control subjects (ages 23 to 34) matches with the other sample classes in Table 2.

The results of this study show that VOC expression in exhaled breath is dramatically altered by COVID-19, with significantly higher total signal, number, and concentration of VOCs in subjects diagnosed with COVID-19 (FIG. 3(*a-c*)). Unlike previous reported results, a large number of statistically significant VOCs (41) were identified by use of the GC-MS QTOF technique coupled to collection through a viral filter into breath bags. Interestingly, many of these VOCs by themselves could distinguish COVID-19 with ROC AUC values>0.80 (FIG. 3(*d*)). Even though acetone and isopropanol have been reported to be biomarkers of many different human conditions[28-30], this study did not identify any significant differences in these analytes when comparing COVID-19 and Control samples.

The VOCs identified as potential biomarkers in this study align broadly with expected VOC metabolites of viral replication and immune response to COVID-19. Close to 50% of the VOCs identified to be differentially expressed were volatile terpenes/terpenoids (VTs) or their esters. These VTs were significantly upregulated. VTs are biosynthesized via the mevalonate pathway through a series of reactions between geranyl pyrophosphate (GPP) and farnesyl pyrophosphate (FPP). Interestingly, preliminary in silico experiments have shown the potential for COVID-19 to dysregulate the mevalonate pathway[31]. Additionally, cholesterol and other steroids are biological products downstream of the mevalonate pathway and have been previously shown to be required components for viral replication as they are the main constituents of viral membranes[16]. Cholesterol and the mevalonate pathway play an important part not only in viral synthesis, but also in viral entry and fusion to host cells. Thus, the alterations in the mevalonate pathway induced by COVID-19 can be reasonably understood to reflect SARS-CoV-2 viral replication[31,32].

Additionally, volatile aldehydes and ketone production are implicated as a potential source of biomarkers for COVID-19. Volatile ketones and aldehydes are closely related to higher oxidation rates of fatty acids[33] and biosynthesis of monofunctional aldehydes is accomplished through the reduction of hydroperoxides by cytochrome P450 through oxidizing poly unsaturated fatty acids (PUFAs)[34-36]. These results correlate with previous literature showing an immune response leads to an increase in oxidative stress which is associated with COVID-19[18,19].

Esters were identified to be a rich source of biomarkers for COVID-19 in this study, especially for the COVID 2 subgroup. In fact, the top four VOCs that are differentiable by COVID subgroup are all acetic acid esters, and all demonstrate $p<0.01$ between COVID 1 and COVID 2. Interestingly, esters and other oxygenated VOCs have been previously demonstrated to be potential biomarkers for influenza by in vitro analyses[37]. The presence of esterified VOCs suggests that perhaps the VOCs, in the lungs of the COVID 2 subjects, were experiencing a strongly oxidative environment, but other explanations are certainly possible. The lower presence of esters in the COVID 1 subgroup also suggests esters alone are poor choices for COVID-19 diagnostic testing but may be useful in a multivariate classification model and/or for prognostic purposes. More robust biological rationales for why exhaled VOC profiles change due to COVID-19 could be provided in future studies by correlating changes in breath to other metabolites, proteins, genes, and transcription factors using a multiple "omic" approach. These approaches could aid with COVID-19 mitigation and may lead to novel and state-of-the-art preventative strategies.

The COVID-19 subjects displayed VOC heterogeneity that caused those samples to cluster, or self-segregate, into two separate groups (COVID 1 and COVID 2). These groups could be separated both on the hierarchical clustergram (FIG. 4(*a*)), and by PCA (FIG. 4(*b*), (*d*)). The COVID 2 subgroup had higher number of VOCs present and higher TUS, while symptoms at time of consent, although trending higher, were not statistically significant, making a correlation between the subgroups and symptoms somewhat equivocal, especially as the cases were, for the most part, relatively mild. However, two of the COVID-19 subjects were hospitalized after donating breath samples, and both belonged to the COVID 2 subgroup. Cycle threshold (viral load) data for this sample cohort were not collected. Another hypothesis is that the VOC heterogeneity might be due to the presence of two different COVID-19 variants within this sample cohort. Unfortunately, genome sequencing was not undertaken to distinguish variants. Therefore, there is no robust scientific rationale for the observation of two COVID subgroups, highlighting the need for more subjects and clinical data to better understand this result.

Interestingly, the separation of subjects into COVID 1 and COVID 2 on the clustergram led to recognition of a separation of the VOCs on the clustergram by functional group.

In fact, both PCA and the clustergrams segregate the VOCs by functional group. These approaches cluster terpenes and ketones/aldehydes together and esters with alkanes (FIG. 4(*a,c,e*)). Esters and alkanes, more prevalent in the middle section of the clustergram, are far more concentrated in COVID 2 than COVID 1, whereas the terpenes and ketones/aldehydes are largely seen in the bottom and top sections of the clustergram. The bottom and top sections of the clustergram show greater similarity between response from COVID 1 and COVID 2.

All multivariate classification models suffer from the possibility of overfitting the data to generate a targeted outcome. Ideally, the results would have been initially generated in a training sample set and independently tested in an alternative validation set to optimally evaluate the performance of the classification model. This is a robust technique to evaluate the true predictive capability of the VOC biosignature. In this study however, too few of samples were collected to stratify the data into separate training and validation cohorts. Therefore, alternatives to independent testing in these cases include cross validation and functional perturbation[38, 39]. When performing cross validation, 1,000 iterations were implemented using different partition schemes to produce a realistic evaluation of performance. In addition to cross validation and functional perturbation, the COVID-19 Recovery sample cohort served as an independent validation cohort, but only to evaluate diagnostic specificity as COVID-19 positive patients were not included in testing. Linear discriminant analysis coupled to forward feature selection identified a panel of three VOCs (FIG. 5) which could distinguish COVID-19 from Control samples with very high cross validated accuracy (>95%). While a fully independent sample cohort including subjects both positive and negative for COVID-19 was not available, 11 of the 14 COVID-19 subjects were able to be reconsented and their breath taken to analyze specificity as a validation cohort. None of the recovered subjects who donated second breath samples had yet been vaccinated for COVID-19, so we cannot report the effect of vaccination on VOC levels. Interestingly, the Recovery (validation) cohort has a similar determination of accuracy (over 90%) as the rigorous data and functional perturbation techniques that were implemented. Both the validation cohort and the statistical analyses show that the classification model of the three VOC biomarkers is robust and should make reliable predictions in future investigations.

Furthermore, this result also shows that VOCs dysregulated by a viral infection are restored to baseline healthy levels upon recovery. COVID-19 Recovery samples in this cohort reported full recovery and at the time of the second collection had not experienced any long-term effects from COVID-19. The VOCs within the COVID-19 Recovery samples for this study showed large differences relative to the COVID-19 samples, and therefore are potentially useful markers for COVID-19 in the acute phase. It would be fruitful to probe VOC differences within the COVID-19 Recovered sample class, as breath VOCs may be useful for predicting if patients diagnosed with COVID-19 will experience long-term effects. This could be accomplished in future longitudinal studies with larger sample cohorts and breath samples taken at multiple points in time after COVID-19 diagnosis and recovery. Potential volatile biomarkers for COVID-19 identified in this study are different than those identified in previous literature by different MS techniques[21-25]. Those studies detected smaller molecules than those found through our extraction/cryotransfer method, and they also found medium chain aldehydes and esters; our method was sensitive enough to detect different medium chain aldehydes and esters, as well as many terpenes, terpenoids, and hydrocarbons.

Conclusion

Figure 6:
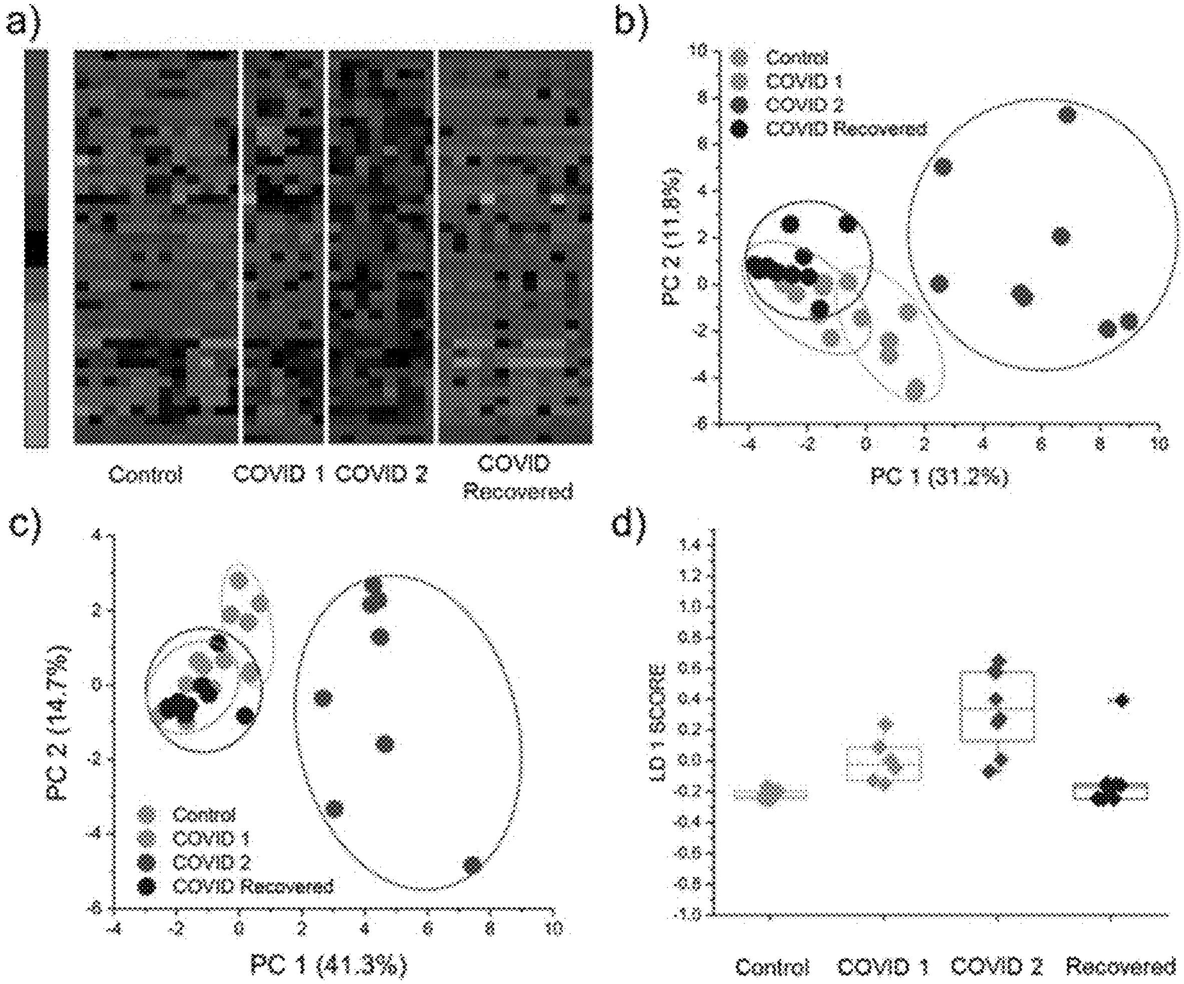
FIG. 6 sets forth the following: (a) Heatmap showing the VOCs detected in COVID Recovered samples are expressed at relatively similar levels when compared to Control samples. PCA separating Control, COVID 1, COVID 2 and COVID Recovered with very high accuracy using VOCs with (b) p-value<0.05 and (c) p-value<0.01. COVID Recovered samples in both PCA plots cluster to a high degree with Control samples. (d) The LDA model developed in FIG. 5 utilized to independently test COVID Recovered samples. COVID Recovered samples highly clustered with Control samples and were distinguished from COVID-19 samples with >90% specificity.

After analysis of 26 subjects (14 with COVID, 12 Control) principal component analysis (PCA) of the top VOCs with the lowest p-values showed COVID samples were naturally separated into two groups labeled COVID 1 (subjects with fewer symptoms) and COVID 2 (subjects with more symptoms). Along the first two principal components, both COVID subgroups could be separated from Control (FIG. 6(*c*)). Supervised machine learning coupled with linear discriminant analysis (LDA) was employed to identify a smaller panel of VOCs which can distinguish COVID-19 with high accuracy. A set of just 3 VOCs separated the healthy Controls from subjects with COVID-19 with a cross validated accuracy >95% (FIG. 6(*d*)). A hierarchical heatmap of the VOCs with the lowest p-values ($p<0.05$) are shown in FIG. 6(*a*). The most striking result came after the subjects with COVID-19 (both COVID 1 and COVID 2) recovered and donated a second breath sample two months after their initial diagnosis. Comparison of the breath of healthy subjects (Control) and those recovered from COVID-19 (COVID Recovered) showed VOCs altered by illness return to baseline healthy levels. This study showed that VOCs are highly dysregulated in symptomatic subjects diagnosed with COVID-19 sheltering at home, which over the course of the pandemic has been the most prevalent response. All subjects contacted from both groups reported full recovery. The results from this study show that specific VOCs noninvasively expressed in breath have the capability of distinguishing COVID-19 symptomatic patients with high accuracy. These results can be utilized to manufacture integrated gas sensors operable to detect the unique VOC biomarkers of COVID-19 with high sensitivity and selectivity for point of care diagnostics.

Figure 7:
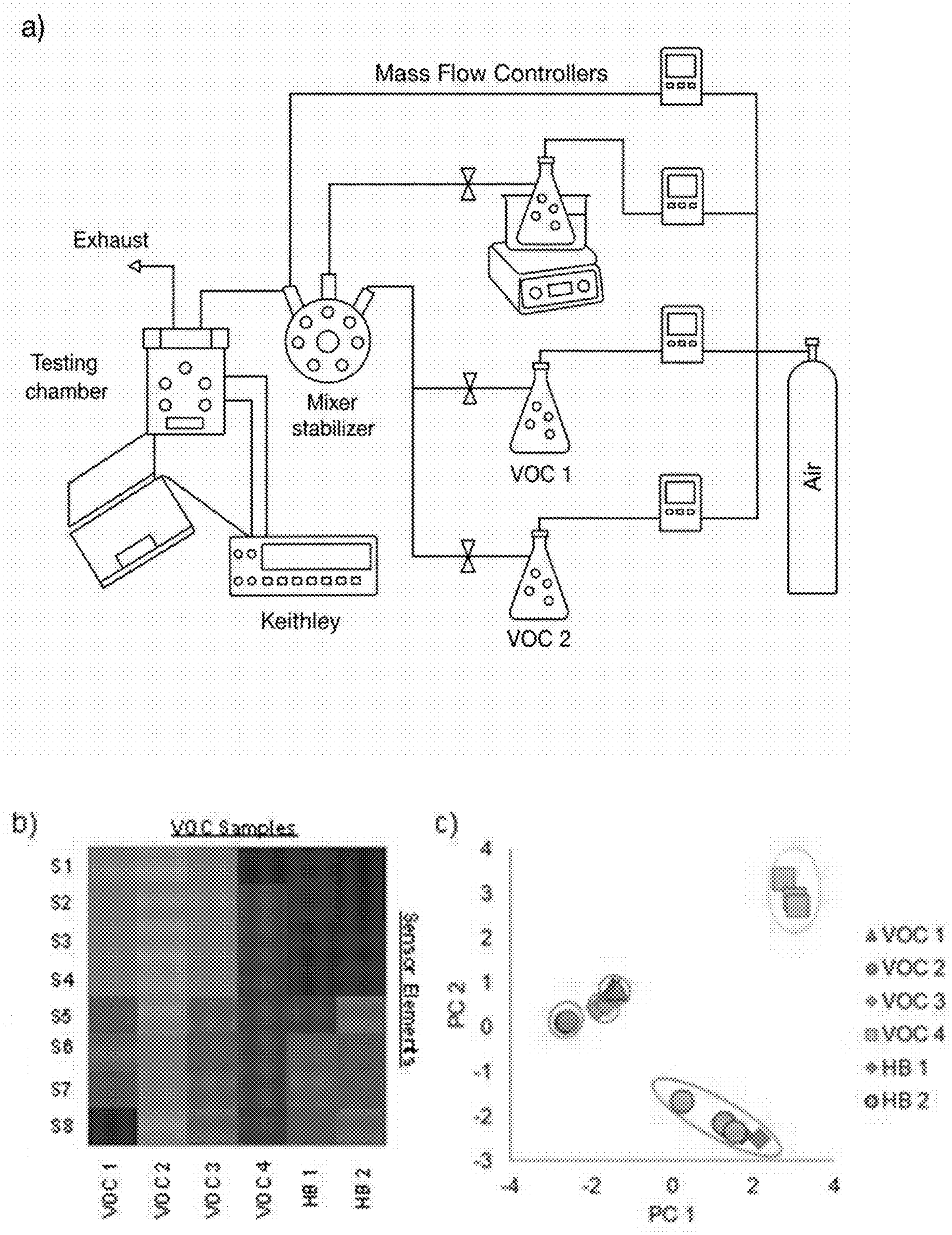
FIG. 7 sets forth the following: (a) Setup for testing nanosensor array response to VOCs. (b) Heatmap showing nanosensor array outputs for VOCs at 6 ppm concentration and human breath (HB 1 and HB 2). (c) Corresponding PCA result.
Figure 8:
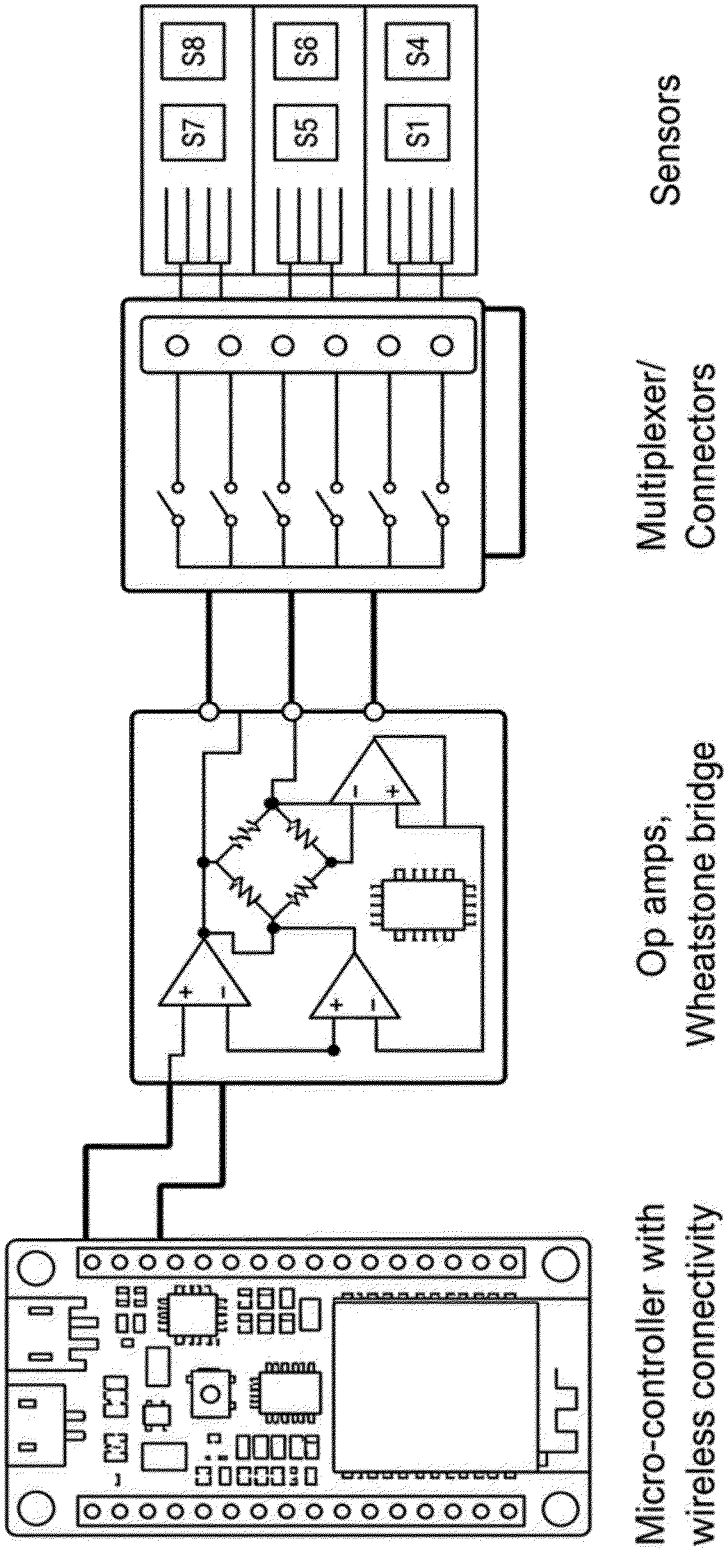
FIG. 8 depicts a schematic representation of a breathalyzer-type device for detecting VOCs associated with COVID-19 infection in a subject.
Figure 9:
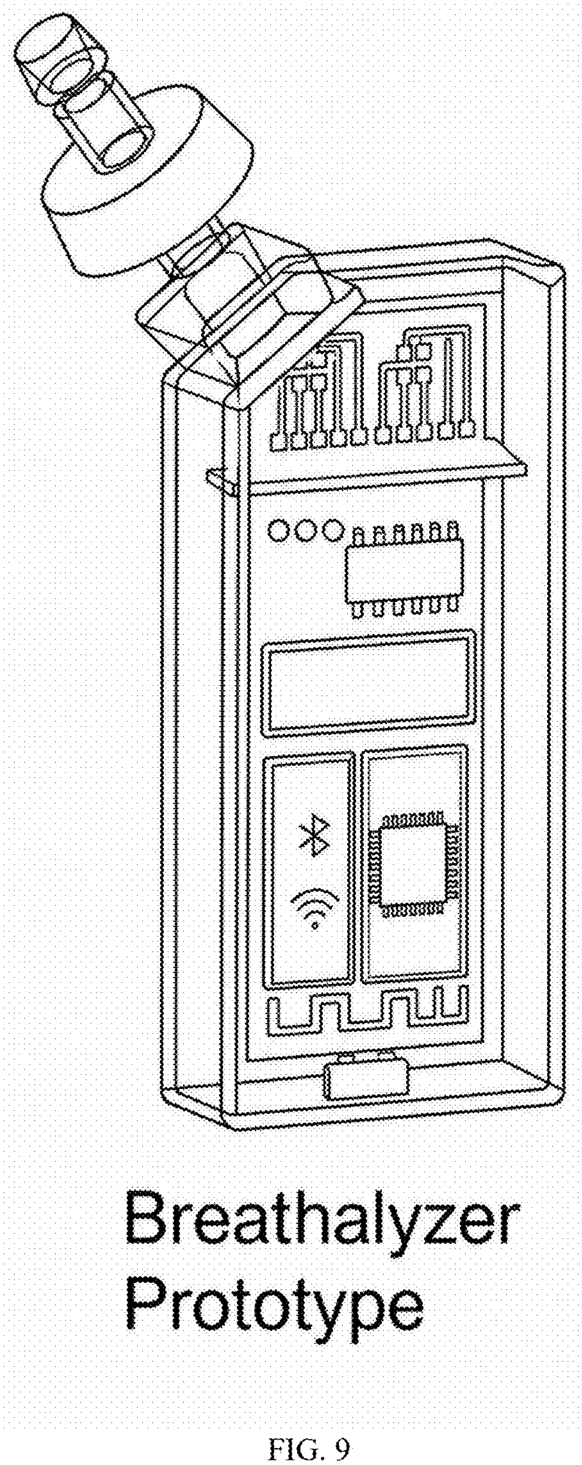
FIG. 9 depicts a prototype breathalyzer-type device for detecting VOCs associated with COVID-19 infection in a subject.

The results from this study can be leveraged for future applications to detect COVID-19 VOC biomarkers in breath. The VOC biomarkers and functional groups identified can be utilized to design a sensitive and selective breathalyzer that can be implemented to detect persons infected with COVID-19. These results are already being used for the design of a portable, accurate and integrated sensor array to monitor individuals for COVID-19 in real-time without the need for single-use reagents. FIG. 7 and FIG. 8. These devices could be utilized to screen individuals for COVID-19 at public locations such as airports, stores, theaters, office settings or in the home of the patient. Previously published results on a multiplexed nanosensor array that could detect persons diagnosed with COVID-19 based on breath analysis could only distinguish COVID-19 with a validated accuracy of 76%[40]. This may be due to the fact that COVID-19 biomarkers were not identified prior to sensor design and fabrication. Devices can be designed to be more accurate in the future by tuning the sensors in the array toward the specific VOC biomarkers of COVID-19.

REFERENCES

1. Allam, M.; Cai, S.; Ganesh, S.; Venkatesan, M.; Doodhwala, S.; Song, Z.; Hu, T.; Kumar, A.; Heit, J.; Study Group, C.; Coskun, A. F., COVID-19 Diagnostics, Tools, and Prevention. Diagnostics (Basel, Switzerland) 2020, 10 (6).
2. Nagura-Ikeda, M.; Imai, K.; Tabata, S.; Miyoshi, K.; Murahara, N.; Mizuno, T.; Horiuchi, M.; Kato, K.; Imoto, Y.; Iwata, M.; Mimura, S.; Ito, T.; Tamura, K.; Kato, Y., Clinical Evaluation of Self-Collected Saliva by Quantitative Reverse Transcription-PCR (RT-qPCR), Direct RT-qPCR, Reverse Transcription-Loop-Mediated Isothermal Amplification, and a Rapid Antigen Test To Diagnose COVID-19. J Clin Microbiol 2020, 58 (9).
3. Scohy, A.; Anantharajah, A.; Bodéus, M.; Kabamba-Mukadi, B.; Verroken, A.; Rodriguez-Villalobos, H., Low performance of rapid antigen detection test as frontline testing for COVID-19 diagnosis. Journal of clinical virology: the official publication of the Pan American Society for Clinical Virology 2020, 129, 104455.
4. Jendrny, P.; Schulz, C.; Twele, F.; Meller, S.; von Köckritz-Blickwede, M.; Osterhaus, A.; Ebbers, J.; Pilchovi, V.; Pink, I.; Welte, T.; Manns, M. P.; Fathi, A.; Ernst, C.; Addo, M. M.; Schalke, E.; Volk, H. A., Scent dog identification of samples from COVID-19 patients—a pilot study. BMC Infect Dis 2020, 20 (1), 536.
5. Angle, C.; Waggoner, L. P.; Ferrando, A.; Haney, P.; Passler, T., Canine Detection of the Volatilome: A Review of Implications for Pathogen and Disease Detection. 2016, 3 (47).
6. Dorman, D. C.; Foster, M. L.; Fernhoff, K. E.; Hess, P. R., Canine scent detection of canine cancer: a feasibility study. Vet Med (Auckl) 2017, 8, 69-76.
7. Jezierski, T.; Walczak, M.; Ligor, T.; Rudnicka, J.; Buszewski, B., Study of the art: canine olfaction used for cancer detection on the basis of breath odour. Perspectives and limitations. Journal of breath research 2015, 9 (2), 027001.

8. Silva, C. L.; Perestrelo, R.; Silva, P.; Tomás, H.; Câmara, J. S., Volatile metabolomic signature of human breast cancer cell lines. Scientific reports 2017, 7, 43969.
9. Woollam, M.; Teli, M.; Angarita-Rivera, P.; Liu, S.; Siegel, A. P.; Yokota, H.; Agarwal, M., Detection of Volatile Organic Compounds (VOCs) in Urine via Gas Chromatography-Mass Spectrometry QTOF to Differentiate Between Localized and Metastatic Models of Breast Cancer. Scientific reports 2019, 9 (1), 2526.
10. Woollam, M.; Teli, M.; Liu, S.; Daneshkhah, A.; Siegel, A. P.; Yokota, H.; Agarwal, M., Urinary Volatile Terpenes Analyzed by Gas Chromatography-Mass Spectrometry to Monitor Breast Cancer Treatment Efficacy in Mice. J Proteome Res 2020, 19 (5), 1913-1922.
11. Gao, Q.; Su, X.; Annabi, M. H.; Schreiter, B. R.; Prince, T.; Ackerman, A.; Morgas, S.; Mata, V.; Williams, H.; Lee, W. Y., Application of Urinary Volatile Organic Compounds (VOCs) for the Diagnosis of Prostate Cancer. Clinical genitourinary cancer 2019, 17 (3), 183-190.
12. Khalid, T.; Aggio, R.; White, P.; De Lacy Costello, B.; Persad, R.; Al-Kateb, H.; Jones, P.; Probert, C. S.; Ratcliffe, N., Urinary Volatile Organic Compounds for the Detection of Prostate Cancer. PLoS One 2015, 10 (11), e0143283.
13. Siegel, A. P.; Daneshkhah, A.; Hardin, D. S.; Shrestha, S.; Varahramyan, K.; Agarwal, M., Analyzing breath samples of hypoglycemic events in type 1 diabetes patients: towards developing an alternative to diabetes alert dogs. Journal of breath research 2017, 11 (2), 026007.
14. Abd El Qader, A.; Lieberman, D.; Shemer Avni, Y.; Svobodin, N.; Lazarovitch, T.; Sagi, O.; Zeiri, Y., Volatile organic compounds generated by cultures of bacteria and viruses associated with respiratory infections. Biomedical Chromatography 2015, 29 (12), 1783-1790.
15. Traxler, S.; Bischoff, A. C.; SaB, R.; Trefz, P.; Gierschner, P.; Brock, B.; Schwaiger, T.; Karte, C.; Blohm, U.; Schrader, C.; Miekisch, W.; Schubert, J. K., VOC breath profile in spontaneously breathing awake swine during Influenza A infection. Scientific reports 2018, 8 (1), 14857.
16. Abu-Farha, M.; Thanaraj, T. A.; Qaddoumi, M. G.; Hashem, A.; Abubaker, J.; Al-Mulla, F., The Role of Lipid Metabolism in COVID-19 Virus Infection and as a Drug Target. International journal of molecular sciences 2020, 21 (10).
17. Li, Y.; Zhou, W.; Yang, L.; You, R., Physiological and pathological regulation of ACE2, the SARS-CoV-2 receptor. Pharmacological research 2020, 157, 104833.
18. Dalan, R.; Bornstein, S. R.; El-Armouche, A.; Rodionov, R. N.; Markov, A.; Wielockx, B.; Beuschlein, F.; Boehm, B. O., The ACE-2 in COVID-19: Foe or Friend? Hormone and metabolic research=Hormon- und Stoffwechselforschung=Hormones et metabolisme 2020, 52 (5), 257-263.
19. Perrotta, F.; Matera, M. G.; Cazzola, M.; Bianco, A., Severe respiratory SARS-CoV2 infection: Does ACE2 receptor matter? Respir Med 2020, 168, 105996-105996.
20. Lamote, K.; Janssens, E.; Schillebeeckx, E.; Lapperre, T. S.; De Winter, B. Y.; van Meerbeeck, J. P., The scent of COVID-19: viral (semi-)volatiles as fast diagnostic biomarkers? Journal of breath research 2020, 14 (4), 042001.
21. Ruszkiewicz, D. M.; Sanders, D.; O'Brien, R.; Hempel, F.; Reed, M. J.; Riepe, A. C.; Bailie, K.; Brodrick, E.; Darnley, K.; Ellerkmann, R.; Mueller, O.; Skarysz, A.; Truss, M.; Wortelmann, T.; Yordanov, S.; Thomas, C. L. P.; Schaaf, B.; Eddleston, M., Diagnosis of COVID-19 by analysis of breath with gas chromatography-ion mobility spectrometry—a feasibility study. EClinicalMedicine 2020, 29.
22. Grassin-Delyle, S.; Roquencourt, C.; Moine, P.; Saffroy, G.; Carn, S.; Heming, N.; Fleuriet, J.; Salvator, H.; Naline, E.; Couderc, L.-J., Metabolomics of exhaled breath in critically ill COVID-19 patients: A pilot study. EBioMedicine 2021, 63, 103154.
23. Steppert, C.; Steppert, I.; Sterlacci, W.; Bollinger, T., Rapid detection of SARS-CoV-2 infection by multicapillary column coupled ion mobility spectrometry (MCC-IMS) of breath. A proof of concept study. Journal of breath research 2021.
24. Chen, H.; Qi, X.; Zhang, L.; Li, X.; Ma, J.; Zhang, C.; Feng, H.; Yao, M., COVID-19 screening using breath-borne volatile organic compounds. Journal of Breath Research 2021. 2020, 2020.06.21.20136523.
25. Ibrahim, W.; Cordell, R. L.; Wilde, M. J.; Richardson, M.; Carr, L.; Sundari Devi Dasi, A.; Hargadon, B.; Free, R. C.; Monks, P. S.; Brightling, C. E.; Greening, N. J.; Siddiqui, S., Diagnosis of COVID-19 by exhaled breath analysis using gas chromatography-mass spectrometry. ERJ Open Research 2021, 7 (3), 00139-2021.
26. Mochalski, P.; King, J.; Unterkofler, K.; Amann, A., Stability of selected volatile breath constituents in Tedlar, Kynar and Flexfilm sampling bags. The Analyst 2013, 138 (5), 1405-1418.
27. Woollam, M.; Wang, L.; Grocki, P.; Liu, S.; Siegel, A. P.; Kalra, M.; Goodpaster, J. V.; Yokota, H.; Agarwal, M., Tracking the Progression of Triple Negative Mammary Tumors over Time by Chemometric Analysis of Urinary Volatile Organic Compounds. Cancers 2021, 13 (6).
28. Toma, K.; Tsujii, M.; Arakawa, T.; Iwasaki, Y.; Mitsubayashi, K., Dual-target gas-phase biosensor (bio-sniffer) for assessment of lipid metabolism from breath acetone and isopropanol. Sensors and Actuators B: Chemical 2021, 329, 129260.
29. Chien, P.-J.; Suzuki, T.; Tsujii, M.; Ye, M.; Minami, I.; Toda, K.; Otsuka, H.; Toma, K.; Arakawa, T.; Araki, K.; Iwasaki, Y.; Shinada, K.; Ogawa, Y.; Mitsubayashi, K., Biochemical Gas Sensors (Biosniffers) Using Forward and Reverse Reactions of Secondary Alcohol Dehydrogenase for Breath Isopropanol and Acetone as Potential Volatile Biomarkers of Diabetes Mellitus. Analytical Chemistry 2017, 89 (22), 12261-12268.
30. Chatterjee, S.; Castro, M.; Feller, J. F., An e-nose made of carbon nanotube based quantum resistive sensors for the detection of eighteen polar/nonpolar VOC biomarkers of lung cancer. Journal of Materials Chemistry B 2013, 1 (36), 4563-4575.
31. Gomez Marti, J. L.; Wells, A.; Brufsky, A. M., Dysregulation of the mevalonate pathway during SARS-CoV-2 infection: An in silico study. Journal of medical virology 2021, 93 (4), 2396-2405.
32. Casari, I.; Manfredi, M.; Metharom, P.; Falasca, M., Dissecting lipid metabolism alterations in SARS-CoV-2. Progress in Lipid Research 2021, 101092.
33. Janfaza, S.; Khorsand, B.; Nikkhah, M.; Zahiri, J., Digging deeper into volatile organic compounds associated with cancer. Biology methods & protocols 2019, 4 (1), bpz014.
34. Esterbauer, H.; Schaur, R. J.; Zollner, H., Chemistry and biochemistry of 4-hydroxynonenal, malonaldehyde and related aldehydes. Free radical biology & medicine 1991, 11 (1), 81-128.

35. Kinter, M., Analytical technologies for lipid oxidation products analysis. Journal of chromatography. B, Biomedical applications 1995, 671 (1-2), 223-36.
36. Pryor, W. A.; Das, B.; Church, D. F., The ozonation of unsaturated fatty acids: aldehydes and hydrogen peroxide as products and possible mediators of ozone toxicity. Chemical research in toxicology 1991, 4 (3), 341-8.
37. Aksenov, A. A.; Sandrock, C. E.; Zhao, W.; Sankaran, S.; Schivo, M.; Harper, R.; Cardona, C. J.; Xing, Z.; Davis, C. E., Cellular scent of influenza virus infection. Chembiochem: a European journal of chemical biology 2014, 15 (7), 1040-8.
38. He, Z.; Yu, W., Stable feature selection for biomarker discovery. Computational biology and chemistry 2010, 34 (4), 215-25.
39. Xia, J.; Broadhurst, D. I.; Wilson, M.; Wishart, D. S., Translational biomarker discovery in clinical metabolomics: an introductory tutorial. Metabolomics: Official journal of the Metabolomic Society 2013, 9 (2), 280-299.
40. Shan, B.; Broza, Y. Y.; Li, W.; Wang, Y.; Wu, S.; Liu, Z.; Wang, J.; Gui, S.; Wang, L.; Zhang, Z.; Liu, W.; Zhou, S.; Jin, W.; Zhang, Q.; Hu, D.; Lin, L.; Zhang, Q.; Li, W.; Wang, J.; Liu, H.; Pan, Y.; Haick, H., Multiplexed Nanomaterial-Based Sensor Array for Detection of COVID-19 in Exhaled Breath. ACS Nano 2020, 14 (9), 12125-12132.

Example 2

Introduction

The biochemical justification for VOCs as biomarkers of disease is that they are endogenous metabolites and byproducts of pathways uniquely affected as soon as disease begins to take hold[3]. Because symptoms do not develop until sometime after metabolic pathways have been significantly dysregulated, the present work is based on the expectation that VOC biomarkers are present before symptoms develop and therefore can be used for pre-symptomatic disease detection. For example, canines can detect the scent of hypoglycemia in their owners even before the blood sugar drops[4]. Researchers over the past decade have been identifying specific VOC biomarkers for many diseases[5], including viral and respiratory infections[6,7]. VOC biomarker identification is often conducted through solid phase microextraction coupled to gas chromatography-mass spectrometry (SPME GC-MS). VOC detection has been attempted with non-specific gas sensor arrays such as the Cyranose, coupled to pattern recognition/machine learning, to correlate sensor responses with disease via a black box methodology. These off-the-shelf sensor arrays have shown some, but limited success[8]. The current work utilizes a powerful synergetic approach, SPME GC-MS quadrupole time-of-flight (QTOF), to rapidly identify VOC biomarkers associated with COVID-19 disease states, and informed nanosensor arrays developed using quality by design (QbD) principles.

The metabolic response to any viral infection appears to be unique to each virus or viral family: previous research has identified specific VOC patterns that are associated with different viruses, including influenza, respiratory syncytial virus and rhinovirus[10]. SARS-CoV-2 also has its own unique VOC pattern. In fact, we have demonstrated that many alveolar VOCs are dysregulated by COVID-19 and that a unique panel of three VOCs can accurately detect COVID-19, as described in Example 1. Preliminary results developing a gas mixing module capable of testing specific VOCs at very low concentrations demonstrated that an array of metallic oxide nanosensors can detect specific VOCs at ppm levels. For this work, identification of VOCs associated with COVID-19 infection by SPME GC-MS QTOF is coupled with expertise at developing nanosensor arrays and reading their output via artificial intelligence and pattern recognition.

SARS-CoV-2 and other viral infections generate a unique volatile signature composed of byproducts from metabolic pathways that are manipulated to meet the cellular energetic requirements for viral replication, regardless of the presence of traditional patient symptoms. Systems with sensing elements tuned to detect identified VOC biomarkers of a specific disease are able to diagnose the condition with high accuracy. This work (1) validates identified VOC biomarkers of COVID-19 from symptomatic and asymptomatic subjects to confirm the possibility of pre-symptomatic detection, and (2) utilizes a nanosensor array that can detect the volatile biomarkers of disease with high sensitivity/specificity and provide accurate diagnostic results.

Utilizing SPME Coupled to GC-MS OTOF to Validate Specific Viral VOC Biomarkers.

VOCs of disease are a diverse group of chemicals associated with metabolic pathways dysregulated in specific ways by disease. Viruses themselves do not emit VOCs, but viruses induce dramatic alteration in cellular metabolism. Viruses hijack metabolic resources for replication, and induce a mounted host body response. For an example, SARS-CoV-2 is an enveloped virus, and therefore replication requires increased lipid/cholesterol metabolism. On the other hand, SARS-CoV-2 binds to and depletes ACE2, which causes an upregulation of specific metabolites related to oxidative stress. For this study, breath samples are collected from healthy subjects as well as from symptomatic/asymptomatic subjects diagnosed with COVID-19. VOCs identified as potential biomarkers in preliminary studies are targeted for validation in this sample cohort.

Research Design and Methods:

Patient Recruitment and Breath Sampling:

Patients are consented, and breath samples are collected from two sample classes: (1) positive for COVID-19 (symptomatic and asymptomatic), and (2) negative for COVID-19 (asymptomatic). 25 samples from each class are utilized for validating biomarkers by GC-MS, and later another 25 are used for testing the developed prototype nanosensor array as discussed below. Additionally, up to 25 alveolar breath samples for each purpose are collected from subjects diagnosed with Influenza A/B or another virus, to serve as a non-COVID specificity control. Patients undergoing RT-PCR analysis are recruited and consented over the phone. Subjects are recruited with emphasis on mirroring the national racial and ethnic makeup. At the time of collection, subjects breathe through a viral filter into a Tedlar bag. The patient provides slow/deep breaths similar to a breathalyzer test for ethanol detection. The collected VOCs are cryotransferred to 20 mL headspace vials. This method uses a microflow controller to draw the sample from the bag and into the vial filled with glass wool, which is maintained at −40° C. and then stored at −80° C. prior to analysis.

SPME GC-MS OTOF and Targeted VOC Analysis:

SPME coupled to GC-MS QTOF is a sensitive tool for the analysis of VOCs. 40 μL of volatile internal standard (10 parts per million), deuterated hexanal (CDN Isotopes, Point-Claire, Quebec, Canada) are spiked in the samples after cryotransfer for accurate quantification of the VOC biomarkers. The samples are then incubated at 60° C. for 45 min for extraction with a pre-conditioned SPME fiber, using a previously optimized extraction procedure. The SPME fiber is injected into the GC-MS QTOF (Agilent 7890A (GC) and 7200 (QTOF)). Data is spectrally deconvoluted/aligned using Agilent software and the VOCs are identified by the NIST17 library or similar. The VOCs that have previously been identified to be differentially expressed by COVID-19 (see Example 1) are quantified by normalized integrated signal (relative to the internal standard) in each of the samples. The Wilcoxon rank sum test is utilized to analyze significant differences between the sample classes. The study set forth in Example 1 identified 41/221 VOCs with $p<0.05$, and 16 with $p<0.01$ with as few as 26 total samples. If the preliminary models do not yield diagnostic sensitivity and specificity over 95%, machine learning through forward feature selection and/or artificial neural networks is implemented on the VOCs to discover an optimal biosignature that exhibits high diagnostic accuracy in the validation (independent/blind) cohort.

Design, Fabricate and Test a Nanosensor Array Comprised of Sensor Elements that are Able to Detect VOC Biomarkers with >90% Sensitivity and Specificity Current gas sensor arrays utilize cross-selectivity coupled with machine learning to distinguish VOC biomarkers. Most commercially available devices are tailored for environmental applications and analyze gases such as oxygen, toxins, and/or combustibles. To implement sensor arrays for biomedical diagnostics, sensing elements must be tuned or tested for the specific VOC biomarkers of the disease. Identifying the VOC biomarkers of COVID-19 prior to system development enables utilization of sensing elements in the array that are both more sensitive and selective to the biomarkers of COVID-19.

This work utilizes a breathalyzer testing system for analyzing sensor response to VOCs, as shown by the schematic in FIG. 7(*a*). Commercially purchased metallic oxide sensor (MOS) arrays were preliminarily tested on four potential VOC biomarkers of disease (including two of the three VOCs in the biosignature in FIG. 7(*b*)) and breath collected from two healthy subjects. Sensors were exposed to both: 1) pure VOCs (six ppm) at a humidity level corresponding to human breath and 2) actual breath provided by healthy volunteers via deep alveolar breaths for 30 seconds. Both the pure VOCs and the actual breath samples were analyzed by the sensor array in triplicate. A heatmap of the average nanosensor output for four VOCs (VOC 1-4) related to disease and breath samples from the two healthy volunteers (HB 1 and HB 2) is shown in FIG. 7(*b*). Each sensor element (eight total sensors, S1-S8) is shown on the y-axis, and the response to different VOCs are shown as a heatmap, where the eight sensors in the array respond differentially to the four VOCs and the healthy breath samples. PCA demonstrated all four of the VOCs of interest are perfectly distinguished from each other and highly separated from healthy breath. Furthermore, the two breath samples overlap significantly showing the similarity of VOC profiles in the actual breath of healthy subjects. These results show the operability of the nanosensor array to classify VOC biomarkers of COVID-19, and the power of its adaptable design when coupled to sensitive VOC identification.

Research Design and Methods:

Design and Fabrication of Sensor Elements:

Existing MOS for a broad range of VOCs including medium chain aldehydes, esters, and terpenes are developed based on the results described above. Material selection is guided by the specific VOC biomarkers validated by SPME GC-MS/QTOF as discussed above. With the panel of VOC biomarkers validated, experiments modifying nanomaterials are implemented to increase MOS sensitivity/selectivity toward the selected VOCs. Existing MOS arrays are modified to increase sensitivity/selectivity for a given VOC by changing the chemical composition of the material and/or applying different chemical or physical treatments of the surface. Furthermore, metal oxides are composited to increase the sensitivity toward a particular VOC. For example, many researchers have reported lists of different nanomaterials which are sensitive to VOC biomarkers of diseases. Polymer composites[11-14], semi conducting nanotubes[15-18], metallic nanocrystals[19,20], and carbon-based nanomaterials[21,22] have been studied for VOC biomarker detection. Different polymeric coatings (polypyrrole, fullerene, poly(vinylidene fluoridehexafluoropropylene) (PVDF-HFP), polydimethylsiloxane (PDMS), and polyetherimide (PEI)) can increase sensor sensitivity, selectivity, and durability.

Characterization of Sensor Elements:

Materials characterization is performed using a number of techniques: Fourier transform infrared spectroscopy (FTIR) and nuclear magnetic resonance spectroscopy (NMR) for organic chemical composition analysis, atomic force and scanning electron microscopies (AFM and SEM) for particle size and homogeneity; electron dispersion spectroscopy, X-Ray diffraction and X-ray photoelectron spectroscopy (EDS, XRD and XPS) for composition and crystal structure; zetasizer, zeta potential, for the stability of material dispersion; UV-Vis-NIR absorption spectroscopy for optoelectronic properties; and a current-voltage/capacitance-voltage semiconductor characterization instrument for electrical properties.

Testing Nanosensors Individually and in the Prototype Array:

Sensors are initially tested on pure and mixtures of VOCs (at concentrations quantified by GC-MS QTOF), including simulated breath. The VOCs are tested by bubbling pure air (80% nitrogen, 19% oxygen, <1% carbon dioxide) at a fixed flow rate through the targeted VOCs. The resulting gas is mixed with humidified air to appropriate concentrations using mass flow controllers (MFCs). When the VOCs come in contact with the sensing layer, they adsorb and produce a measurable change in current due to the displacement of activated oxygen ions at the sensor surface. The time required to reach 90% of saturation value (response time) and the time required to return to 10% of its value (recovery time) are recorded. Limits of detection and quantitation are calculated by running blank samples and building calibration curves. Reproducibility of a single sensor is tested through repeated exposure of a VOC five times. Reproducibility is also tested among devices fabricated in the same batch and from different batches. Degradation and shelf life is measured by placing a sensor in the test chamber at atmospheric humidity/temperature conditions and measuring responses over two months. Accelerated degradation tests are conducted to determine the lifetime of the sensors.

Pattern Recognition/Training the Prototype Array:

Selectivity to a target VOC is measured by exposing the nanosensors to other VOCs biomarkers, common breath and environmental VOCs. The output of the nanosensor array is initially programmed based on VOC biomarker and simulated breath responses. The effect of using at least four sensors with 90% accuracy and fold change >two suggests that it is straightforward to program the sensor array with machine learning to achieve >98% separation. Actual breath samples (25 from COVID-19 positive symptomatic/asymptomatic and 25 from healthy controls) are collected and transferred from Tedlar bags using MFCs.

REFERENCES

1 Angle, C., Waggoner, L. P., Ferrando, A., Haney, P. & Passler, T. Canine Detection of the Volatilome: A Review of Implications for Pathogen and Disease Detection. 3, doi:10.3389/fvets.2016.00047 (2016).
2 Jezierski, T., Walczak, M., Ligor, T., Rudnicka, J. & Buszewski, B. Study of the art: canine olfaction used for cancer detection on the basis of breath odour. Perspectives and limitations. Journal of breath research 9, 027001, doi:10.1088/1752-7155/9/2/027001 (2015).
3 Janfaza, S., Khorsand, B., Nikkhah, M. & Zahiri, J. Digging deeper into volatile organic compounds associated with cancer. Biology methods & protocols 4, bpz014, doi:10.1093/biomethods/bpz014 (2019).
4 Linebaugh, K. Service Dogs Pick Up Scent of Diabetes Danger. Wall Street Journal (2012).
5 Oakley-Girvan, I. & Davis, S. W. Breath based volatile organic compounds in the detection of breast, lung, and colorectal cancers: A systematic review. Cancer Biomarkers 21, 29-39, doi:10.3233/CBM-170177 (2018).
6 Traxler, S. et al. VOC breath profile in spontaneously breathing awake swine during Influenza A infection. Scientific reports 8, 14857, doi:10.1038/s41598-018-33061-2 (2018).
7 Ruszkiewicz, D. M. et al. Diagnosis of COVID-19 by analysis of breath with gas chromatography-ion mobility spectrometry—a feasibility study. EClinicalMedicine 29, doi:10.1016/j.eclinm.2020.100609 (2020).
8 Wilson, A. D. Applications of Electronic-Nose Technologies for Noninvasive Early Detection of Plant, Animal and Human Diseases. 6, 45 (2018).
9 Tan, J. K. et al. The prevalence and clinical significance of Presymptomatic COVID-19 patients: how we can be one step ahead in mitigating a deadly pandemic. BMC Infectious Diseases 21, 249, doi:10.1186/s12879-021-05849-7 (2021).
10 Lamote, K. et al. The scent of COVID-19: viral (semi-) volatiles as fast diagnostic biomarkers? Journal of breath research 14, 042001, doi:10.1088/1752-7163/aba105 (2020).
11 Fu, D. et al. Polymer coated silicon microring device for the detection of sub-ppm volatile organic compounds. Sensors and Actuators B: Chemical 257, 136-142, doi: https://doi.org/10.1016/j.snb.2017.10.166 (2018).
12 Mgwenya, T. N. Polymer nanocomposites-based sensors for the detection of lung cancer volatile organic biomarkers, University of Johannesburg, (2018).
13 Setka, M., Drbohlavovi, J. & Hubilek, J. Nanostructured Polypyrrole-Based Ammonia and Volatile Organic Compound Sensors. Sensors (Basel) 17, 562, doi:10.3390/s17030562 (2017).
14 Yavarinasab, A. et al. Graphene/poly (methyl methacrylate) electrochemical impedance-transduced chemiresistor for detection of volatile organic compounds in aqueous medium. Anal Chim Acta 1109, 27-36, doi:10.1016/j.aca.2020.02.065 (2020).
15 Bhattacharyya, D., Kumar, P., Smith, Y. R., Mohanty, S. K. & Misra, M. Plasmonic-enhanced electrochemical detection of volatile biomarkers with gold functionalized TiO2 nanotube arrays. Journal of Materials Science & Technology 34, 905-913, doi:https://doi.org/10.1016/j.jmst.2017.11.010 (2018).
16 Park, C. H., Schroeder, V., Kim, B. J. & Swager, T. M. Ionic Liquid-Carbon Nanotube Sensor Arrays for Human Breath Related Volatile Organic Compounds. ACS Sens 3, 2432-2437, doi:10.1021/acssensors.8b00987 (2018).
17 Prasongkit, J., Tangsukworakhun, S., Jaisutti, R. & Osotchan, T. Highly sensitive and selective sensing of acetone and hydrogen sulfide using metal phthalocyanine-carbon nanotube hybrids. Applied Surface Science 532, 147314, doi:https://doi.org/10.1016/j.apsusc.2020.147314 (2020).
18 Sachan, A., Castro, M., Choudhary, V. & Feller, J.-F. Influence of Water Molecules on the Detection of Volatile Organic Compounds (VOC) Cancer Biomarkers by Nanocomposite Quantum Resistive Vapor Sensors vQRS. 6, 64 (2018).
19 Matatagui, D. et al. Chemoresistive gas sensor based on ZIF-8/ZIF-67 nanocrystals. Sensors and Actuators B: Chemical 274, 601-608, doi:https://doi.org/10.1016/j.snb.2018.07.137 (2018).
20 Wang, D. et al. Bimetallic PtCu Nanocrystal Sensitization WO(3) Hollow Spheres for Highly Efficient 3-Hydroxy-2-butanone Biomarker Detection. ACS Appl Mater Interfaces 12, 18904-18912, doi:10.1021/acsami.0c02523 (2020).
21 Bahoumina, P. et al. in 2017 Symposium on Design, Test, Integration and Packaging of MEMS/MOEMS (DTIP). 1-4.
22 Tung, T. T. et al. Carbon nanomaterial sensors for cancer and disease diagnosis. 167-202 (2019).

All documents cited herein are hereby expressly incorporated by reference herein in their entireties. Referenced materials are not admitted prior art.

As will be appreciated from the descriptions herein, a wide variety of aspects and embodiments are contemplated by the present disclosure, examples of which include, without limitation, the aspects and embodiments listed below:

In a first aspect, either alone or in combination with any other aspect, a method for diagnosing a subject for a COVID-19 infection state includes collecting an exhaled breath sample from a subject; passing the breath sample into contact with a volatile organic compound (VOC) sensor operable to detect at least one VOC biomarker for a COVID-19 infection state; producing a readable sensor output for the at least one VOC biomarker; and diagnosing the COVID-19 infection state of the subject based on the readable sensor output.

In a second aspect, either alone or in combination with any other aspect, the sensor comprises a GC-MS.

In a third aspect, either alone or in combination with any other aspect, the sensor comprises a GC-MS QTOF.

In a fourth aspect, either alone or in combination with any other aspect, the COVID-19 infection state comprises a state selected from the group consisting of COVID-19 Negative and COVID-19 Positive.

In a fifth aspect, either alone or in combination with any other aspect, the COVID-19 infection state comprises a state selected from the group consisting of COVID-19 Negative, COVID-19 Positive Symptomatic and COVID-19 Positive Asymptomatic.

In a sixth aspect, either alone or in combination with any other aspect, the at least one VOC biomarker is selected from the group consisting of an ester having a molecular weight of less than 200 g/mol, an aldehyde and a terpene.

In a seventh aspect, either alone or in combination with any other aspect, the ester is selected from the group consisting of Acetic Acid, hexyl ester; 3,5,5-Trimethylhexyl acetate; Bicyclo[2.2.1]heptan-2-ol, 1,3,3-trimethyl-, acetate, (1S-exo)-; 4-tert-Butylcyclohexyl acetate; Benzenemethanol, alpha-methyl-, acetate; alpha-Terpinyl acetate, isomers thereof; and combinations of two or more thereof.

In an eighth aspect, either alone or in combination with any other aspect, the aldehyde is selected from the group consisting of Hexanal, 3,5,5-trimethyl-; 5-Heptenal, 2,6-dimethyl; isomers thereof; and a combination of two or more thereof.

In a ninth aspect, either alone or in combination with any other aspect, the terpene is selected from the group consisting of o-Cymene; Eucalyptol; alpha-Bisabolene; beta-Bourbonene; alpha-Phellandrene; alpha-Cedrene; Dihydromyrcenol; 3-Thujene; Terpinene; Linalool; D-Limonene; Camphor; 1-Menthone; Copaene; Terpinen-4-ol; Caryophyllene; 3-carene; and a combination of two or more thereof.

In a tenth aspect, either alone or in combination with any other aspect, the at least one VOC biomarker is selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In an eleventh aspect, either alone or in combination with any other aspect, the at least one VOC biomarker comprises at least two unsaturated terpenes, each having 5, 10 or 15 carbons, and at least one aldehyde.

In a twelfth aspect, either alone or in combination with any other aspect, the at least one VOC biomarker comprises at least three VOCs wherein at least two of the VOCs are terpenes.

In a thirteenth aspect, either alone or in combination with any other aspect, the at least one VOC biomarker comprises at least three VOCs wherein at least one of the VOCs is a terpene and at least one of the VOCs is an aldehyde or a ketone.

In a fourteenth aspect, either alone or in combination with any other aspect, the at least one VOC biomarker comprises at least three VOCs wherein at least one of the VOCs is an aldehyde and at least one of the VOCs is a ketone.

In a fifteenth aspect, either alone or in combination with any other aspect, the at least one VOC biomarker comprises at least three VOCs wherein at least one of the VOCs is an aldehyde and at least one of the VOCs is an alcohol.

In a sixteenth aspect, either alone or in combination with any other aspect, the at least one VOC biomarker comprises at least three VOCs wherein at least two of the VOCs are esters and at least one of the VOCs is a terpene.

In a seventeenth aspect, either alone or in combination with any other aspect, the at least one VOC biomarker is selected from the group consisting of comprises at least three VOCs, and wherein at least two of the VOCs are esters and at least one of the VOCs is a terpene.

In an eighteenth aspect, either alone or in combination with any other aspect, each of the esters, terpenes, aldehydes and ketones is selected from Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a nineteenth aspect, either alone or in combination with any other aspect, the at least one VOC biomarker comprises at least three VOCs selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a twentieth aspect, either alone or in combination with any other aspect, the at least one VOC biomarker is selected from the group consisting of hexyl acetate (Acetic Acid, hexyl ester), 3,5,5-trimethyl-hexanal, alpha-cedrene and isomers thereof.

In a twenty-first aspect, either alone or in combination with any other aspect, the at least one VOC biomarker comprises at least two or at least three VOCs selected from the group consisting of hexyl acetate (Acetic Acid, hexyl ester), 3,5,5-trimethyl-hexanal, alpha-cedrene and isomers thereof.

In a twenty-second aspect, either alone or in combination with any other aspect, a COVID-19 infection state COVID-19 Positive correlates to an indication in the readable output sensor representing the presence of at least one VOC biomarker selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a twenty-third aspect, either alone or in combination with any other aspect, the VOC sensor comprises a nanoparticle sensor.

In a twenty-fourth aspect, either alone or in combination with any other aspect, the readable sensor output includes a concentration or amount for the at least one VOC biomarker.

In a twenty-fifth aspect, either alone or in combination with any other aspect, the method further comprises determining a correlation between the readable sensor output and a predefined signal or signal pattern associated with the COVID-19 infection state; and identifying, based at least in part on the determination of a correlation with the predefined signal or signal pattern, the presence of the COVID-19 infection state.

In a twenty-sixth aspect, either alone or in combination with any other aspect, the method further comprises processing the readable sensor output via a neural network or pattern recognition algorithm, wherein the readable sensor output correlates with a predefined signal or signal pattern associated with the COVID-19 infection state; and identifying, based at least in part on the determination of a correlation with the predefined signal or signal pattern, the presence of the COVID-19 infection state.

In a twenty-seventh aspect, either alone or in combination with any other aspect, the VOC sensor comprises a first sensor component operable to expose one or more nanoparticles to a first one of the at least one VOC biomarker in the alveolar air breath sample, wherein the one or more nanoparticles are operable to react to a presence of or contact with the first of the at least one VOC biomarker; a second sensor component operable to generate an electronic signal when the one or more nanoparticles react to the presence of or contact with the first of the at least one VOC biomarker, wherein the electronic signal is associated with a concentration or amount of the first of the plurality of VOC biomarkers; and an electronic circuit operable to transmit the electronic signal to an output device or computer processor.

In a twenty-eighth aspect, either alone or in combination with any other aspect, the sensor comprises an array of sensor subunits, each sensor subunit operable to detect at least one of the at least one VOC biomarker.

In a twenty-ninth aspect, either alone or in combination with any other aspect, a system for detecting and identifying at least one VOC biomarker for a COVID-19 infection state in exhaled breath of a subject, the system comprising: a mouth piece connected to a housing, the mouth piece operable to receive the exhaled breath of the subject; a sensor module disposed in the housing, the sensor module operable to detect the at least one VOC biomarker in the exhaled breath, and further operable to produce a readable sensor output for the at least one VOC biomarker; and a communication module disposed in the housing and in communication with the sensor module, the communication module operable to transmit collected data from the sensor module.

In a thirtieth aspect, either alone or in combination with any other aspect, the sensor module comprises at least one array of sensor subunits, wherein each sensor subunit is operable to detect at least one VOC biomarker.

In a thirty-first aspect, either alone or in combination with any other aspect, the COVID-19 infection state comprises a state selected from the group consisting of COVID-19 Negative and COVID-19 Positive.

In a thirty-second aspect, either alone or in combination with any other aspect, the COVID-19 infection state comprises a state selected from the group consisting of COVID-19 Negative, COVID-19 Positive Symptomatic and COVID-19 Positive Asymptomatic.

In a thirty-third aspect, either alone or in combination with any other aspect, the at least one VOC biomarker is selected from the group consisting of an ester having a molecular weight of less than 200 g/mol, an aldehyde and a terpene.

In a thirty-fourth aspect, either alone or in combination with any other aspect, the ester is selected from the group consisting of Acetic Acid, hexyl ester; 3,5,5-Trimethylhexyl acetate; Bicyclo[2.2.1]heptan-2-ol, 1,3,3-trimethyl-, acetate, (1S-exo)-; 4-tert-Butylcyclohexyl acetate; Benzenemethanol, alpha-methyl-, acetate; alpha-Terpinyl acetate, isomers thereof; and combinations of two or more thereof.

In a thirty-fifth aspect, either alone or in combination with any other aspect, the aldehyde is selected from the group consisting of Hexanal, 3,5,5-trimethyl-; 5-Heptenal, 2,6-dimethyl; isomers thereof; and a combination of two or more thereof.

In a thirty-sixth aspect, either alone or in combination with any other aspect, the terpene is selected from the group consisting of o-Cymene; Eucalyptol; alpha-Bisabolene; beta-Bourbonene; alpha-Phellandrene; alpha-Cedrene; Dihydromyrcenol; 3-Thujene; Terpinene; Linalool; D-Limonene; Camphor; 1-Menthone; Copaene; Terpinen-4-ol; Caryophyllene; 3-carene; and a combination of two or more thereof.

In a thirty-seventh aspect, either alone or in combination with any other aspect, the at least one VOC biomarker is selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a thirty-eighth aspect, either alone or in combination with any other aspect, the at least one VOC biomarker comprises at least two unsaturated terpenes, each having 5, 10 or 15 carbons, and at least one aldehyde.

In a thirty-ninth aspect, either alone or in combination with any other aspect, the at least one VOC biomarker comprises at least three VOCs wherein at least two of the VOCs are terpenes.

In a fortieth aspect, either alone or in combination with any other aspect, the at least one VOC biomarker comprises at least three VOCs wherein at least one of the VOCs is a terpene and at least one of the VOCs is an aldehyde or a ketone.

In a forty-first aspect, either alone or in combination with any other aspect, the at least one VOC biomarker comprises at least three VOCs wherein at least one of the VOCs is an aldehyde and at least one of the VOCs is a ketone.

In a forty-second aspect, either alone or in combination with any other aspect, the at least one VOC biomarker comprises at least three VOCs wherein at least one of the VOCs is an aldehyde and at least one of the VOCs is an alcohol.

In a forty-third aspect, either alone or in combination with any other aspect, the at least one VOC biomarker comprises at least three VOCs wherein at least two of the VOCs are esters and at least one of the VOCs is a terpene.

In a forty-fourth aspect, either alone or in combination with any other aspect, the at least one VOC biomarker is selected from the group consisting of comprises at least three VOCs, and wherein at least two of the VOCs are esters and at least one of the VOCs is a terpene.

In a forty-fifth aspect, either alone or in combination with any other aspect, each of the esters, terpenes, aldehydes and ketones is selected from Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a forty-sixth aspect, either alone or in combination with any other aspect, the at least one VOC biomarker comprises at least three VOCs selected from Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a forty-seventh aspect, either alone or in combination with any other aspect, the at least one VOC biomarker is selected from the group consisting of hexyl acetate (Acetic Acid, hexyl ester), 3,5,5-trimethyl-hexanal, alpha-cedrene; isomers thereof; and a combination of two or more thereof.

In a forty-eighth aspect, either alone or in combination with any other aspect, the at least one VOC biomarker comprises at least two or at least three VOCs selected from the group consisting of hexyl acetate (Acetic Acid, hexyl ester), 3,5,5-trimethyl-hexanal, alpha-cedrene; isomers thereof; and a combination of two or more thereof.

In a forty-ninth aspect, either alone or in combination with any other aspect, a COVID-19 infection state COVID-19 Positive correlates to an indication in the readable output sensor representing the presence of at least one VOC biomarker selected from the group consisting of Acetic Acid, hexyl ester; Hexanal, 3,5,5-trimethyl-; o-Cymene; Eucalyptol; 3,5,5-Trimethylhexyl acetate; Bicyclo[2.2.1]heptan-2-ol, 1,3,3-trimethyl-, acetate, (1S-exo)-; Cyclohexane, 2-butyl-1,1,3-trimethyl-; Linalool; 1-Decanol, 2-ethyl-; alpha-Bisabolene; 2-Octanone; alpha-Cedrene; 5-Heptenal, 2,6-dimethyl-; beta-Bourbonene; alpha-Phellandrene; Nonane, 2,2,4,4,6,8,8-heptamethyl-; Dihydromyrcenol; 3-Thujene; Terpinene; Hexane, 3,4-bis(1,1-dimethylethyl)-2,2,5,5-tetramethyl-; Benzene, 1,3-dichloro-; Hexane, 1-(hexyloxy)-5-methyl-; Nonane, 3,7-dimethyl-; D-Limonene; Camphor; Dodecane, 2,7,10-trimethyl-; Hexadecane; 4-tert-Butylcyclohexyl acetate; 3-Undecene, 5-methyl-; alpha-Terpinyl acetate; 3-carene; 1-Menthone; Copaene; Undecane, 2,3-dimethyl-; Diethyl Phthalate; Terpinen-4-ol; Toluene; 2-Undecene, 9-methyl-; Caryophyllene; Benzenemethanol, alpha-methyl-, acetate; isomers thereof; and a combination of two or more thereof.

In a fiftieth aspect, either alone or in combination with any other aspect, the sensor module comprises at least one nanoparticle sensor.

In a fifty-first aspect, either alone or in combination with any other aspect, the readable sensor output includes a concentration or amount for the at least one VOC biomarker.

In a fifty-second aspect, either alone or in combination with any other aspect, the communication module is further operable to transmit collected data via at least one of the following: IR (infrared) communication, wireless communication, a Bluetooth protocol wireless communication, a direct wired connection, or to a remote memory storage device.

In a fifty-third aspect, either alone or in combination with any other aspect, the system further comprises a biomarker processing module in communication with the sensor module, the biomarker processing module operable to process the collected data associated with detection of the at least one VOC biomarker and to identify the at least one VOC biomarker.

In a fifty-fourth aspect, either alone or in combination with any other aspect, the biomarker processing module is further operable to process the collected data via a neural network or pattern recognition algorithm, wherein a result from the biomarker processing module is received by the communication module for output to a software application loaded on a computer or a hand-held electronic device.

In a fifty-fifth aspect, either alone or in combination with any other aspect, the biomarker processing module is further operable to process the collected data in conjunction with other sensor data, wherein a result from the biomarker processing module is received by the communication module for output to a software application loaded on a computer or a hand-held electronic device.

In a fifty-sixth aspect, either alone or in combination with any other aspect, the software application is operable to communicate the collected data to a health care provider to facilitate tracking of the collected data.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

All publications, patents, and patent applications referenced herein are hereby incorporated by reference in their entirety for all purposes as if each publication, patent, or patent application had been individually indicated to be incorporated by reference.

What is claimed is:

1. A method for diagnosing a subject for a COVID-19 infection state, comprising:

collecting an exhaled breath sample from a subject;

passing the breath sample into contact with a volatile organic compound (VOC) sensor operable to detect at least one VOC biomarker for a COVID-19 infection state;

producing a readable sensor output for the at least one VOC biomarker; and diagnosing the COVID-19 infection state of the subject based on the readable sensor output, wherein a first one of the at least one VOC biomarker includes a terpene, and wherein the terpene is selected from the group consisting of o-Cymene; Eucalyptol; alpha-Bisabolene; beta-Bourbonene; alpha-Phellandrene; alpha-Cedrene; Dihydromyrcenol; 3-Thujene; Terpinene; Linalool; D-Limonene; Camphor; 1-Menthone; Copaene; Terpinen-4-ol; Caryophyllene; 3-carene; and a combination of two or more thereof.

2. The method of claim 1 wherein the sensor comprises a GC-MS.

3. The method of claim 2 wherein the sensor comprises a GC-MS QTOF.

4. The method of claim 1 wherein a second one of the at least one VOC biomarker includes an ester having a molecular weight of less than 200 g/mol or an aldehyde.

5. The method of claim 4 wherein the ester is selected from the group consisting of Acetic Acid, hexyl ester; 3,5,5-Trimethylhexyl acetate; Bicyclo[2.2.1]heptan-2-ol, 1,3,3-trimethyl-, acetate, (1S-exo)-; 4-tert-Butylcyclohexyl acetate; Benzenemethanol, alpha-methyl-, acetate; alpha-Terpinyl acetate, isomers thereof; and combinations of two or more thereof.

6. The method of claim 4 wherein the aldehyde is selected from the group consisting of Hexanal, 3,5,5-trimethyl-; 5-Heptenal, 2,6-dimethyl; isomers thereof, and a combination of two or more thereof.

7. The method of claim 1 wherein a second one of the at least one VOC biomarker comprises an unsaturated terpene, having 5, 10 or 15 carbons, and wherein a third one of the at least one VOC biomarker comprises an aldehyde.

8. The method of claim 1 wherein a second one of the at least one VOC biomarker comprises a terpenes.

9. The method of claim 1 wherein a second one of the at least one VOC biomarker comprises an aldehyde or a ketone.

10. The method of claim 1 wherein a second one of the at least one VOC biomarker comprises an aldehyde, and wherein a third one of the at least one VOC biomarker comprises a ketone.

11. The method of claim 1 wherein a second one of the at least one VOC biomarker comprises an aldehyde, and wherein a third one of the at least one VOC biomarker comprises an alcohol.

12. The method of claim 1 wherein a second one of the at least one VOC biomarker comprises a first ester, and wherein a third one of the at least one VOC biomarker comprises a second ester.

13. The method of claim 1, further comprising:

determining a correlation between the readable sensor output and a predefined signal or signal pattern associated with the COVID-19 infection state; and identifying, based at least in part on the determination of a correlation with the predefined signal or signal pattern, the presence of the COVID-19 infection state.

14. The method of claim 1, further comprising:

processing the readable sensor output via a neural network or pattern recognition algorithm, wherein the readable sensor output correlates with a predefined signal or signal pattern associated with the COVID-19 infection state; and identifying, based at least in part on the determination of a correlation with the predefined signal or signal pattern, the presence of the COVID-19 infection state.

15. The method of claim 1 wherein the VOC sensor comprises a first sensor component operable to expose one or more nanoparticles to the first one of the at least one VOC biomarker in the alveolar air breath sample, wherein the one or more nanoparticles are operable to react to a presence of or contact with the first of the at least one VOC biomarker; a second sensor component operable to generate an electronic signal when the one or more nanoparticles react to the presence of or contact with the first of the at least one VOC biomarker, wherein the electronic signal is associated with a concentration or amount of the first of the plurality of VOC biomarkers; and an electronic circuit operable to transmit the electronic signal to an output device or computer processor.

16. A system for detecting and identifying at least one VOC biomarker for a COVID-19 infection state in exhaled breath of a subject, the system comprising:

a mouth piece connected to a housing, the mouth piece operable to receive the exhaled breath of the subject;

a sensor module disposed in the housing, the sensor module operable to detect the at least one VOC biomarker in the exhaled breath, and further operable to produce a readable sensor output for the at least one VOC biomarker; and a communication module disposed in the housing and in communication with the sensor module, the communication module operable to transmit collected data from the sensor module, wherein a first one of the at least one VOC biomarker includes a terpene, and wherein the terpene is selected from the group consisting of o-Cymene; Eucalyptol; alpha-Bisabolene; beta-Bourbonene; alpha-Phellandrene; alpha-Cedrene; Dihydromyrcenol; 3-Thujene; Terpinene; Linalool; D-Limonene; Camphor; 1-Menthone; Copaene; Terpinen-4-ol; Caryophyllene; 3-carene; and a combination of two or more thereof.

17. The system of claim 16, wherein the sensor module comprises at least one array of sensor subunits, wherein each sensor subunit is operable to detect the at least one VOC biomarker.

18. The system of claim 16 wherein a second one of the at least one VOC biomarker includes an ester having a molecular weight of less than 200 g/mol or an aldehyde.

19. The system of claim 16, further comprising a biomarker processing module in communication with the sensor module, the biomarker processing module operable to process the collected data associated with detection of the at least one VOC biomarker and to identify the at least one VOC biomarker.

20. The system of claim 19, wherein the biomarker processing module is further operable to process the collected data in conjunction with other sensor data, wherein a result from the biomarker processing module is received by the communication module for output to a software application loaded on a computer or a hand-held electronic device.

* * * * *